(12) United States Patent
Sedaghati et al.

(10) Patent No.: US 11,435,345 B2
(45) Date of Patent: Sep. 6, 2022

(54) DETECTION AND TREATMENT OF DEMYELINATING DISEASES

(71) Applicant: MATN SCIENTIFIC LIMITED, Hemel Hempstead (GB)

(72) Inventors: Mahmoud Sedaghati, Tehran (IR); Mahsa Sedaghati, San Francisco, CA (US); Tina Sedaghati, London (GB)

(73) Assignee: MATN SCIENTIFIC LIMITED, Hemel Hempstead (GB)

( * ) Notice: Subject to any disclaimer, the term of this patent is extended or adjusted under 35 U.S.C. 154(b) by 125 days.

(21) Appl. No.: 16/346,478

(22) PCT Filed: Nov. 1, 2017

(86) PCT No.: PCT/EP2017/077968
§ 371 (c)(1),
(2) Date: Apr. 30, 2019

(87) PCT Pub. No.: WO2018/083124
PCT Pub. Date: May 11, 2018

(65) Prior Publication Data
US 2019/0257830 A1      Aug. 22, 2019

(30) Foreign Application Priority Data
Nov. 1, 2016  (GB) .................... 1618432

(51) Int. Cl.
| *G01N 33/564* | (2006.01) |
| *C07K 14/47* | (2006.01) |
| *C07K 7/08* | (2006.01) |
| *A61K 39/00* | (2006.01) |
| *C07K 4/00* | (2006.01) |
| *A61K 38/00* | (2006.01) |

(52) U.S. Cl.
CPC ....... *G01N 33/564* (2013.01); *A61K 39/0008* (2013.01); *C07K 4/00* (2013.01); *C07K 7/08* (2013.01); *C07K 14/4713* (2013.01); *A61K 38/00* (2013.01); *G01N 2800/285* (2013.01)

(58) Field of Classification Search
CPC ............... A61K 38/00; A61K 39/0008; C07K 14/4713; C07K 4/00; C07K 7/08; G01N 2800/285; G01N 33/564
See application file for complete search history.

(56) References Cited

U.S. PATENT DOCUMENTS

| 2004/0043431 A1 | 3/2004 | Vojdani | |
| 2004/0248795 A1 | 12/2004 | Guttman | |
| 2005/0037422 A1 | 2/2005 | Ben-Nun et al. | |
| 2006/0258576 A1 | 11/2006 | Immonen et al. | |
| 2007/0048329 A1 | 3/2007 | Khanna et al. | |
| 2010/0322945 A1* | 12/2010 | Timmerman | C07K 14/7158 424/152.1 |
| 2015/0322137 A1 | 11/2015 | Takada et al. | |

FOREIGN PATENT DOCUMENTS

| EP | 1452868 A2 | 9/2004 |
| WO | 01/31019 A2 | 5/2001 |
| WO | 01/31021 A1 | 5/2001 |
| WO | 02/069232 A2 | 9/2002 |
| WO | 03/106491 A2 | 12/2003 |
| WO | 2007/064941 A2 | 6/2007 |
| WO | 2008/109833 A2 | 9/2008 |
| WO | 2009/011572 A1 | 1/2009 |
| WO | 2009/068627 A2 | 6/2009 |
| WO | 2010/074821 A1 | 7/2010 |
| WO | 2011/085081 A2 | 7/2011 |
| WO | 2011/092253 A1 | 8/2011 |
| WO | 2012/056407 A1 | 5/2012 |
| WO | 2012/057624 A1 | 5/2012 |
| WO | 2012/098089 A1 | 7/2012 |
| WO | 2012/159079 A1 | 11/2012 |
| WO | 2013/112922 A1 | 8/2013 |
| WO | 2014/115893 A1 | 7/2014 |
| WO | 2016/032977 A1 | 3/2016 |
| WO | 2016/172722 A1 | 10/2016 |
| WO | 2016/187216 A1 | 11/2016 |

OTHER PUBLICATIONS

David Miller, The differential diagnosis of multiple sclerosisiMcAlpine's Multiple Sclerosis. 2006 : 389-437. Published online May 15, 2009, pp. 389-437.*
Trotter, John L., et al. "HPRT mutant T-cell lines from multiple sclerosis patients recognize myelin proteolipid protein peptides." Journal of neuroimmunology 75.1-2 (1997): 95-103.
Tuohy, Vincent K., et al. "Diversity and plasticity of self recognition during the development of multiple sclerosis." The Journal of clinical investigation 99.7 (1997): 1682-1690.
Miura, Yoshiro, and Shuichi Seto. "Synthesis of a Fragment (Pentapeptide) of E. coli Acyl Carrier Protein Apoprotein." Bulletin of the Chemical Society of Japan 42.12 (1969): 3592-3593.
Greenfield, Edward A., et al. "Monoclonal antibodies to distinct regions of human myelin proteolipid protein simultaneously recognize central nervous system myelin and neurons of many vertebrate species." Journal of neuroscience research 83.3 (2006): 415-431.
Timmerman, Peter, Wouter C. Puijk, and Rob H. Meloen. "Functional reconstruction and synthetic mimicry of a conformational epitope using CLIPS™ technology." Journal of Molecular Recognition: An Interdisciplinary Journal 20.5 (2007): 283-299.
Foroughipour, Azam, et al. "Evaluating sex hormone levels in reproductive age women with multiple sclerosis and their relationship with disease severity." Journal of research in medical sciences: the official journal of Isfahan University of Medical Sciences 17.9 (2012): 882-885.

(Continued)

*Primary Examiner* — Julie Ha
*Assistant Examiner* — Erinne R Dabkowski
(74) *Attorney, Agent, or Firm* — Meunier Carlin & Curfman LLC

(57) ABSTRACT

The present invention relates to methods of detecting, diagnosing and distinguishing between demyelinating diseases such as Multiple Sclerosis. The present invention also relates to methods of treating, and peptides for use in the treatment of, demyelinating diseases such as Multiple Sclerosis.

16 Claims, 13 Drawing Sheets

Specification includes a Sequence Listing.

(56) References Cited

OTHER PUBLICATIONS

Mix, Eilhard, et al. "Animal models of multiple sclerosis—potentials and limitations" Progress in neurobiology 92.3 (2010): 386-404.
International Search Report and Written Opinion. PCT Application No. PCT/EP2017/077968. Issued by the International Searching Authority (EP) dated Jan. 24, 2018. 25 pages.
International Preliminary Report on Patentability. PCT Application No. PCT/EP2017/077968. Issued by the International Preliminary Examining Authority dated Mar. 20, 2019. 15 pages.

* cited by examiner

Reactivation of
Astrocytes : leading to
plaque formation

| Investigated | Note | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|---|---|---|---|---|---|---|---|---|
| Pseudomonas putida | 1 | S | R | L | T | L | S | P | E | Q | A | H | S | L | I | L | Q | H | L |
| HCG 40453 - IFIT1 | 2 | H | M | P | R | T | Q | E | N | A | H | S | L | E | R | C | W | L |
| PLP1 | 3 | P | R | G | S | R | G | Q | H | Q | A | H | S | L | E | R | V | C | H |
| FSH | 4 | F | R*- | V | p* | G | C | A | H | H | A*- | D-* | S*- | L*- | Y | T | L*- | Y* | P | V |
| Human herpesvirus 4- protein 1 | 5 | E | R | H | S | D | E | H | H | H | D | D | S | L | P | H | P | Q | Q |
| Anti-idiotype antibody | 6 | A | R | D | S | A | N | I | Y | H | A | D | S | L | K | G | R | F | T |
| | | | | | | | | | | | | | | | | | | | |
| Not investigated | | | | | | | | | | | | | | | | | | | |
| HCG 1659014 | | R | L | G | T | H | V | L | E | A | H | S | L | D | K | V | S | H |
| Streptomyces cattleya (1) | | R | I | G | A | E | S | H | H | A | D | A | L | Q | | | | |
| Streptomyces aurantiacus (2) | | R | M | S | T | P | N | P | H | A | D | S | L | | | | | |
| Helicobacter pylori | | S | S | P | E | H | R | L | A | H | S | L | E | R | D | Y | G |

| | | | | | | | | | A | D | S | L | | | | | |
|---|---|---|---|---|---|---|---|---|---|---|---|---|---|---|---|---|---|
| R | X | S | X | X | X | X | X | H | A | D | X | L | X | X | X | X | X |
| R | X | P | X | X | X | X | X | H | X | D | X | L | X | X | X | X | X |
| R | X | S | X | X | X | X | X | H | X | D | S | L | X | X | X | X | X |
| R | X | S | X | X | X | X | X | H | A | D | S | L | X | X | X | X | X |
| R | X | P | X | X | X | X | X | H | A | D | S | L | X | X | X | X | X |
| R | X | S | X | X | X | X | X | Q | A | H | S | L | X | X | X | X | X |
| R | X | P | X | X | X | X | X | Q | A | H | S | L | X | X | X | X | X |
| | X | S | X | X | X | X | X | Q | A | H | S | L | X | X | X | X | X |
| | | | | | | | | | A | H | S | L | | | | | |

Figure 13

DETECTION AND TREATMENT OF DEMYELINATING DISEASES

RELATED APPLICATIONS

This application is a national stage application filed under 35 U.S.C. § 371 of PCT/EP2017/077968, which claims priority from GB1618432.7, the content of which is hereby expressly incorporated by reference in its entirety.

REFERENCE TO SEQUENCE LISTING

The Sequence Listing submitted Mar. 22, 2021, as a text file named "10480-004US1_2021_03_22_Sequence_Listing.txt," created on Mar. 22, 2021, and having a size of 19 kilobytes is hereby incorporated by reference pursuant to 37 C.F.R. § 1.52(e)(5).

FIELD OF THE INVENTION

The present invention relates to methods of detecting, diagnosing and distinguishing between demyelinating diseases such as Multiple Sclerosis. The present invention also relates to methods of treating, and compositions for use in the treatment of, demyelinating diseases such as Multiple Sclerosis.

BACKGROUND OF THE INVENTION

Demyelinating diseases are conditions in which the myelin sheath of neurons is damaged. In some demyelinating diseases, termed inflammatory demyelinating diseases (IDDs), autoimmune reactions are thought to be involved in the myelin damage associated with disease. Devic's disease (neuromyelitis optica) is one example of inflammatory demyelinating diseases, which manifests as an inflamed and demyelinated optic nerve.

In contrast, leukodystrophies, also known as dysmyelinating diseases, are genetic disorders characterized by degeneration of myelin. One example is Pelizaeus-Merzbacher disease (PMD), in which a mutation in a myelin protein called proteolipid protein 1 (PLP1) cause the inability of the myelin formation. In some forms of these diseases, part of PLP is not produced.

Multiple Sclerosis (MS) is a demyelinating disease which manifests as a lifelong neurological condition. An estimated 2.5 million people suffer from MS worldwide, with more than 127,000 people in the UK in 2010, and this number is growing by approximately 2.4% per year. The MS incidence is reported as 165, 140, 174, and 212 (per 100,000) in England, Wales, Northern Ireland, and Scotland, respectively (1,2). MS is also widely considered to be an IDD, although several theories exist as to the mechanism underlying demyelination and inflammation in MS. The damage to the central nerves system (CNS) in MS seems to be due to the immune system mistakenly attacking the myelin sheath (i.e., an autoimmune attack), thereby affecting the brain and spinal cord. Other theories including damage to, or deficiency of, the myelin-producing cells. The cause of the demyelination seen in MS is unknown.

The diagnosis of demyelinating diseases such as MS often takes many years, there are many variables involved and there is no single pattern to the disease. The underlying cause of MS is believed to be a combination of genetic, immunological and environmental factors. However, as disease progression and the course of the disease is unpredictable, until now it has been impossible to determine a specific cause or trigger.

The following observations have been made about the symptoms and incidence of MS:
- The number and position of lesions on a patient's central nervous system does not necessarily correlate with their relapse occurrence or level of disability
- The most common MS symptoms are fatigue, pain, bladder and bowel issues, sexual dysfunction, movement and coordination problems, visual problems and cognition and emotional changes
- MS is about two times more prevalent in women than in men
- MS is the most common disease of the CNS in young adults, mostly diagnosed in their 20-30s
- MS is not directly hereditary, although genetic susceptibility plays a part in its development
- MS is not contagious or infectious
- The incidence of MS increases in countries further from the equator
- Everyone's MS is different, hence no two individuals will have the same range and severity of symptoms, even if they are closely related.

Currently, there are no symptoms, physical findings or laboratory tests that can conclusively prove or rule out MS. The diagnostic process currently involves a combination of examinations:
- Neurological examination: the neurologist looks for evidence of two or more areas of scarring in different parts of the central nervous system that have occurred at different points in time.
- Blood test: while there is no definitive blood test for MS, blood tests are often used to rule out other conditions that cause symptoms similar to those of MS.
- Magnetic resonance imaging (MRI): the scars caused by MS show up as white patches, giving a clear picture of the effects of MS on the brain and spinal cord.
- Lumbar puncture: inserting a hollow needle into the base of the spine and drawing off a sample of cerebrospinal fluid (CSF) for analysis.
- Evoked potentials: to measure the speed of nerve messages along sensory nerves to the brain. Delays in messages, which are often not apparent to the individual being tested, can indicate that there is damage to the nerve pathway.

No individual symptom is unique to the condition, which means that in order to reach a diagnosis, a range of other possible explanations have to be ruled out, resulting in a lengthy diagnosis process.

Current Treatments

There is currently no cure for MS. A limited number of treatments are available to manage MS symptoms and their impacts on a patient's life by modifying the course of the disease. Disease modifying drugs can reduce the frequency and severity of relapses, but are not effective in treating primary progressive MS. The only available treatments aim to alleviate symptoms, for instance medication for seizures. Although research into genetic and stem cell treatments of demyelinating diseases is ongoing, no effective treatments of the underlying diseases are currently available.

SUMMARY OF THE INVENTION

The inventors have identified peptide antigens from diverse proteins that play an important role in MS development. Based on these findings, the present invention provides assays, which can quantify the level of particular antibodies in blood samples and which can be used to distinguish demyelination disease patients from subjects that do not have a demyelinating disease, such as patients that have a dysmyelinating disease. Based on these findings, the present inventors also provide novel animal models of demyelinating diseases and novel therapies for demyelinating diseases.

The central feature of the invention is a 4-amino acid (aa) motif. In some of the proteins that play an important role in MS development, the 4-aa motif is present as an "AHSL" motif. In other proteins that play an important role in MS development, the 4-aa motif is present as an "ADSL" or a "DDSL" motif.

Accordingly, in a first aspect, the invention provides an oligopeptide comprising the sequence "ADSL" (SEQ ID NO: 4).

The 4-aa motif of the invention (ADSL) belongs to a broader class of oligopeptides comprising the sequence "$Z^1Z^2SL$" (SEQ ID NO: 1). In most embodiments, residue "$Z^1$" represents "A" (alanine), so the oligopeptide of the invention comprises the sequence "$AZ^2SL$" (SEQ ID NO: 2). In other embodiments, residue "$Z^1$" represents "D" (aspartic acid), so the oligopeptide of the invention comprises the sequence "$DZ^2SL$" (SEQ ID NO: 3). In some embodiments, residue "$Z^2$" is "D" (aspartic acid), so the oligopeptide of the invention comprises the sequence "ADSL" (SEQ ID NO: 4). In other embodiments, residue "$Z^2$" is "H" (histidine), so the oligopeptide of comprises the sequence "AHSL" (SEQ ID NO: 5).

The 4-aa motif of the invention may be provided as a tetrapeptide, having only 4 amino acid residues (and not comprising any further amino acid residue). Alternatively, the 4-aa motif may be provided as part of longer a oligopeptide, e.g. 12-mer, 17-mer, or an oligopeptide of any length as described herein.

In preferred embodiments of the invention, the oligopeptide comprises an arginine residue at a position that is towards the N-terminus of the oligopeptide from the "$Z^1Z^2SL$" motif, and separated by 7 intervening amino acids from the "$Z^1$" residue of the "$Z^1Z^2SL$" motif. In other words, some embodiments of the invention comprise the sequence "$RXXXXXXXZ^1Z^2SL$" (SEQ ID NO: 7) wherein "X" represents any natural or unnatural amino acid residue. In some embodiments, the amino acid sequence of the oligopeptide consists of SEQ ID NO: 7, although it may include other (non-peptide) chemical or physical moieties.

In some embodiments of the invention, the amino acid sequence "$Z^1Z^2SL$" (SEQ ID NO: 1) is part of the sequence "$HZ^1Z^2SL$" (SEQ ID NO: 8) (such that the oligopeptide comprises the amino acid sequence "$HZ^1Z^2SL$"). In other words, some embodiments of the invention comprise the sequence HADSL (SEQ ID NO: 48). In other embodiments, the amino acid sequence "$Z^1Z^2SL$" (SEQ ID NO: 1) or "$AZ^2SL$" (SEQ ID NO: 2) is part of the sequence "$QZ^1Z^2SL$" (SEQ ID NO: 9) (such that the oligopeptide comprises the amino acid sequence "$QZ^1Z^2SL$"). In some embodiments, the amino acid sequence of the oligopeptide consists of SEQ ID NO: 8 or 9, although it may include other (non-peptide) chemical or physical moieties.

The skilled person will appreciate that the embodiments of the invention can be combined. For instance, the sequence of SEQ ID NO: 7 can be combined with of SEQ ID NOs: 8 or 9. The oligopeptides of those embodiments respectively comprise the sequence "$RXXXXX HZ^1Z^2SL$" (SEQ ID NO: 10) or "$RXXXXXXQZ^1Z^2SL$" (SEQ ID NO: 11).

In some embodiments of the invention, the oligopeptide comprises the amino acid sequence "$Z^1Z^2SLE$" (SEQ ID NO: 12). In some embodiments of the invention, the oligopeptide comprises the amino acid sequence "$Z^1Z^2SLXR$" (SEQ ID NO: 13). Some embodiments of the invention comprise the amino acid sequence "$Z^1Z^2SLER$" (SEQ ID NO: 34) and some embodiments of the invention comprise the amino acid sequence "$RXXXXXXXZ^1Z^2SLER$" (SEQ ID NO: 35). Those oligopeptides of the inventions that include glutamic acid "E" at 'position 13' and include arginine "R" at 'position 14', e.g. SEQ ID NOs: 34 and 35, are particularly important in the context of the therapeutic aspects of this invention.

In some embodiments of the invention, the oligopeptide comprises amino acid sequence "$SXXXXXZ^1Z^2SL$" (SEQ ID NO: 14). In some embodiments, the oligopeptide comprises amino acid sequence "$PXXXXXZ^1Z^2SL$" (SEQ ID NO: 15). In other words, the oligopeptide of the invention may comprise amino acid sequence SXXXXXADSL (SEQ ID NO: 49) or amino acid sequence PXXXXXADSL (SEQ ID NO: 50). In some embodiments, the oligopeptide has between 12-17 amino acids. For instance, the oligopeptide of the invention may have 12 amino acids, or the oligopeptide of the invention may have 17 amino acids. In some embodiments, the oligopeptide comprises or consists of amino acid sequence "$RXXXXXXXZ^1Z^2SLXXXXX$" (SEQ ID NO: 17). Residue "X" represents any natural amino acid residue or an unnatural amino acid residue.

In some embodiments, the amino acid sequence of the oligopeptide of the invention consists of any one of SEQ ID NOs: 8-17, although it may include other (non-peptide) chemical or physical moieties.

In some embodiments of this disclosure, the amino acid sequence "$DZ^2SL$" (SEQ ID NO: 3) is "DDSL" (SEQ ID NO: 6). In other embodiments, the amino acid sequence "$DZ^2SL$" is "DHSL" (SEQ ID NO: 16).

As also shown in FIG. 13, one oligopeptide of the invention has the sequence "RLTLSPEQAHSLILQHL" (SEQ ID NO: 18), which is denoted antigen "S". Another oligopeptide of the invention has the sequence "MPRTQENAHSLERCWL" (SEQ ID NO: 19), which is denoted antigen "H". Another oligopeptide of the invention has the sequence "RGSRGQHQAHSLERVCH" (SEQ ID NO: 20), which is denoted antigen "P". Another oligopeptide of the invention has the sequence "RVPGCAHHADSLYTYPV" (SEQ ID NO: 21), which is denoted antigen "F". Another oligopeptide of the invention has the sequence "RHSDEHHHDDSLPHPQQ" (SEQ ID NO: 22), which is denoted antigen "E". Another oligopeptide of the invention has the sequence "RDSANIYHADSLKGRFT" (SEQ ID NO: 23), which is denoted antigen "A". Another oligopeptide of the invention has the sequence "RLGTHVLEAHSLDKVSH" (SEQ ID NO: 24). Another oligopeptide of the invention has the sequence "RMSTPNPHADSL" (SEQ ID NO: 25). Another oligopeptide of the invention has the sequence "SSPEHRLAHSLERDYG" (SEQ ID NO: 26).

In some embodiments, the oligopeptide of the invention has the sequence RLTLSPEQAHSL (SEQ ID NO: 27), RGSRGQHQAHSL (SEQ ID NO: 28), RVPGCAHHADSL (SEQ ID NO: 29), RHSDEHHHDDSL (SEQ ID NO: 30), RDSANIYHADSL (SEQ ID NO: 31), RLGTHVLEAHSL (SEQ ID NO: 32) or RMSTPNPHADSL (SEQ ID NO: 33).

In another aspect, the invention provides nucleic acids encoding the oligopeptides of the invention. The nucleic acid may be a vector, which itself may be comprised within a host cell. The oligopeptide of the invention may be expressed by the host cell comprising the nucleic acid of the invention. The nucleic acid of the invention is capable of expressing the oligopeptide in a host cell. This distinguishes the nucleic acid of the invention from genomic nucleic acid sequences which may express the amino acid motifs of the invention, but as part of larger proteins, not as part of an oligopeptide.

As described herein, the oligopeptide of the invention can be used in applications related to the diagnosis and treatment of demyelinating diseases such as MS. The inventors have demonstrated that the oligopeptides of the invention can be used in methods of measuring the levels of certain antibodies in a sample from a subject. The inventors have also found that these antibodies are of diagnostic significance for demyelinating diseases such as multiple sclerosis (MS).

Accordingly, in a second aspect, the invention provides in vitro methods for measuring the level, in a sample, of antibody that binds to the oligopeptides of the invention. This method comprises providing the oligopeptide immobilized on a substrate, bringing the sample and the substrate into contact with each other, and measuring the level of antibody bound to the substrate.

In some embodiments, the oligopeptide is conjugated to a first member of a specific binding pair and the substrate comprises the second member of the specific binding pair, such that the oligopeptide has been immobilized on the substrate by bringing the first member and the second member of the specific binding pair into contact with each other. The specific binding pair may be comprised of biotin and streptavidin or a protein that is functionally equivalent to streptavidin because it is also capable of binding biotin. In some embodiments, the first member of the specific binding pair (that is conjugated to the oligopeptide of the invention) is biotin. The substrate may be an ELISA plate. The substrate may be a magnetic bead. The sample may be a serum sample that has been obtained from a human subject.

The oligopeptides of the invention (e.g. SEQ ID NO: 27-32) can induce MS, to various severity, in both male and female gender. Among these sequences, those having 'D' amino acid at position $Z^2$ are more effective. Amongst antigen sequences with 'D' amino acid at $Z^2$, antigens F and A (SEQ ID NOs: 21 and 23) are particularly effective in the in vitro method for measuring the level of antibody when the sample is taken from a male subject. Oligopeptides with SEQ ID NO: 29 and 31 are also preferred in the in vitro method for measuring the level of antibody when the sample is taken from a male subject.

Therefore, in the in vitro method for measuring the level of antibody that binds to the oligopeptides of the invention in a sample, the subject may be a male subject and the oligopeptide may have a sequence that is selected from the group consisting of (SEQ ID NO: 21), (SEQ ID NO: 23), (SEQ ID NO: 29), and (SEQ ID NO: 31).

In the in vitro method for measuring the level of antibody that binds to the oligopeptides of the invention in a sample, the subject may be a female subject and the oligopeptide antigens P and E (SEQ ID NOs: 20 and 22) are the best sequences. Oligopeptides with SEQ ID NO: 28 and 30 are also preferred in the in vitro method for measuring the level of antibody when the sample is taken from a female subject. Therefore in the in vitro method for measuring the level of antibody that binds to the oligopeptides of the invention in a sample, the subject may be a female subject and the oligopeptide may have a sequence that is selected from the group consisting of (SEQ ID NO: 20), (SEQ ID NO: 22), (SEQ ID NO: 28), and (SEQ ID NO: 30).

In some embodiments, the in vitro method further comprises the step of comparing the level of antibody that binds the oligopeptide of the invention with a control level which is representative of the level of antibody that binds the oligopeptide in a healthy subject. In some embodiments, a lower level of antibody that binds the oligopeptide in the sample, compared with the control level of antibody that binds the oligopeptide, is indicative of a demyelinating disease such as multiple sclerosis (MS). The level of antibody may be used to distinguish between a leukodystrophy and a demyelinating disease such as multiple sclerosis (MS) in a patient with a disease of the myelin sheath.

In some embodiments, the part of the in vitro method involving binding the antibody to the oligopeptide is performed at a pH of approximately 7.1 (e.g. between pH 7.05 to pH 7.15). In other embodiments, the part of the in vitro method involving binding the antibody to the oligopeptide is performed at a pH of approximately 7.4 (e.g. between pH 7.35 to pH 7.45). In embodiments where the binding the antibody to the oligopeptide is performed at a pH of approximately 7.1 (i.e., the sample is buffered to a pH of approximately 7.1, e.g. pH 7.05 to pH 7.15), the level of antibody in MS patient samples is often found to be higher than the level of antibody in control samples. In contrast, in embodiments where the binding the antibody to the oligopeptide is performed at a pH of approximately 7.4 (i.e., the sample is buffered to a pH of approximately 7.4, e.g. pH 7.35 to pH 7.45), the level of antibody in MS patient samples is often found to be lower than the level of antibody in control samples.

In some embodiments, the in vitro method comprises measuring the level of antibody that binds a first oligopeptide of the invention, and the method further comprises measuring the level of antibody that binds a second oligopeptide of the invention.

In a related (third) aspect, kits for performing the in vitro methods for measuring antibody levels in a sample as described herein are also provided. The kit will contain required components to perform the described methods, and may further comprise additional components such as syringes, test tubes, and/or an instruction page.

In a fourth aspect, the invention provides a method of inducing a disease of the myelin sheath in a non-human animal, the method comprising administering to the non-human animal both an oligopeptide of the invention and an adjuvant. In some embodiments, the adjuvant is Freund's complete adjuvant. The oligopeptide and the adjuvant may be administered at the same time. The oligopeptide and the adjuvant may be administered by intradermal injection. In some embodiments, the induced disease of the myelin sheath is characteristic of a demyelinating disease such as multiple sclerosis (MS). In most embodiments, plaque formation is induced in the brain of the non-human animal. In some embodiments, plaque formation is induced without substantial damage to the blood brain barrier (BBB). In some embodiments, the method also comprises administering Pertussis toxin to the non-human animal. The non-human animal may be a mouse, a rat, a guinea pig, a pig, a cow, a cat, a chicken or any other animal with PLP sequence (for the sequence alignment of PLP and other lipophilins in various species see FIG. 16.2 of reference (20)). In some embodiments, the weight of the non-human animal is reduced following administration of the oligopeptide of the invention. In some embodiments, the animal is sacrificed following disease induction and the number of plaques in a mid-brain section the animal (which is taken as representative of number of plaques in the rest of the brain) is higher than the number of plaques in a mid-brain section of equivalent size in a control animal of the same type that has not undergone disease induction as described herein. In some embodiments, the animal exhibits lowered muscular function compared with the muscular function of a control animal of the same type that has not undergone disease induction as described herein, as measured by an objective muscle function test such as the fall-from-ring test or the fall-from-inverted-cage test.

In a related (fifth) aspect, the invention provides an animal that is a model of a demyelinating disease in humans, wherein the animal has a demyelinating disease that has been induced according to the fourth aspect of the invention. The fourth and fifth aspects of the invention provide an invaluable tool for the research of diseases of the myelin sheath that will in likelihood lead to yet further substantial benefits to man.

In a sixth aspect, the invention provides an oligopeptide of the invention for use as a medicament. In a seventh aspect, the invention provides an oligopeptide of the invention for use in diagnostics.

In an eighth aspect, the invention provides an oligopeptide of the invention for use in a method of treating a demyelinating disease in a subject, the method comprising administering the oligopeptide to the subject.

The disease of may be an inflammatory demyelinating diseases (IDDs) such as multiple sclerosis (MS). In some embodiments, the disease is primary progressive MS. Preferably, the oligopeptide is administered intravenously, orally, intranasally or via an aerosol.

Preferably the subject is a human subject. The oligopeptide of the invention may be administered to the subject more than once. For instance, the oligopeptide of the invention may be administered every day, e.g. once per day or twice per day. Alternatively, the oligopeptide of the invention may be administered weekly or twice per week or three times per week. Alternatively, oligopeptide of the invention may be administered once or twice per month.

A dosage of the oligopeptide of the invention may be in the range of 1 mg per dose to 200 mg per dose. For instance, one dose of the oligopeptide of the invention may be 10 mg, 20 mg, 30 mg, 40 mg, 50 mg, 75 mg, 100 mg, or 150 mg per dose.

In a ninth aspect, the invention provides an antibody that specifically binds to the oligopeptide of the invention.

The antibody may be identified by eluting antibody that binds to the substrate of the second and third aspects, and characterising the antibody. The antibody may be a polyclonal antibody. Alternatively, the antibody may be a monoclonal antibody. For instance, an antibody may be identified as described herein, and then cloned and expressed in a hybridoma.

BRIEF DESCRIPTION OF THE FIGURES

FIG. 13. Sequence alignment of exemplary oligopeptides of the invention. The first six oligopeptides, denoted "S", "H", "P", "F", "E" and "A", (corresponding to SEQ ID NOs: 18-23) have been investigated e.g. as described in experimental examples 2-6, below. The remaining oligonucleotides have been identified by way of sequence and literature analysis but have not yet undergone full experimental investigation. FSH represents follicle stimulating hormone.

DETAILED DESCRIPTION

Figure 1:
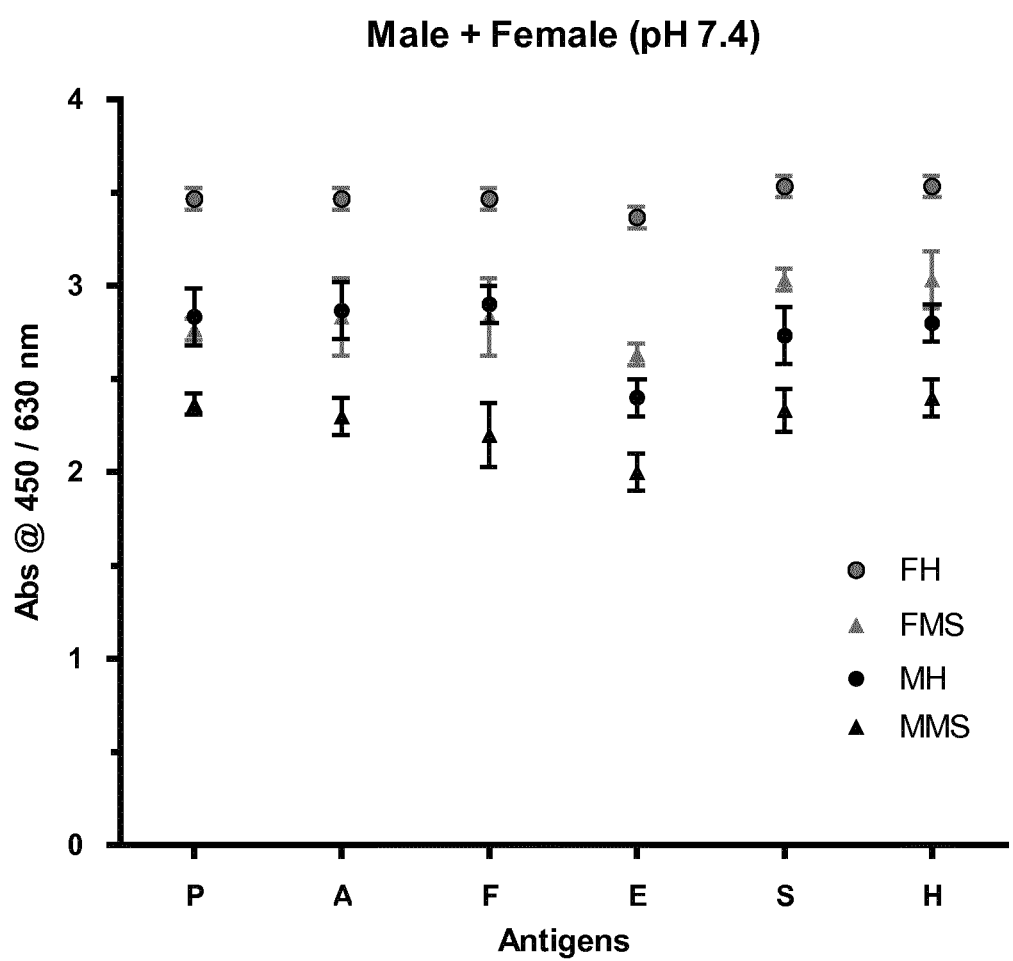
FIG. 1. Diagnostic blood test—ELISA assay on male and female samples at pH 7.4. Antibody levels determined in the blood samples from subjects (both male and female participants). Healthy female patients (HF), female patients with MS (FMS), healthy male patients (HM), male patients with MS (MMS). In healthy subjects, the levels of MS specific antibody is higher in female than male individuals. Antibody levels in FMS are approximately at the same level as healthy male participants (MH).

The following applications of the present invention are provided by way of example and not limitation.

Oligopeptides of the Invention

In embodiments of the invention in which the oligopeptide is longer than 4-aa in length, the inventors have found that the amino acid residues that flank the core $Z^1Z^2SL$ motif are not crucial to the functioning of the invention. FIG. 13 shows the sequence alignment of several oligopeptides of the invention. In the sequence alignment of FIG. 13, the $Z^1Z^2SL$ motif of each oligopeptide is shown at amino acid positions 9, 10, 11 and 12. Taking this numbering, the inventors have found that the identity of the amino acid residues at any of positions 2-8 (when present) is not essential to the functioning of the invention. Either "H" (histidine) or "Q" (glutamine) is preferred at position 8, although this is not essential. Similarly, the inventors found that the amino acid residues at any of positions 13-17 (when present) are not essential to the functioning of the invention, although "E" (glutamic acid) is preferred at position 13 and "R" (arginine) is preferred at position 14 (although neither is essential). However, in embodiments of the invention related to treatment, the presence of "E" at 'position 13' and "R" at 'position 14' is advantageous. The inventors did however find that the amino acid residue at position 1 (when present) should be "R" (arginine).

Preferably, the oligopeptide of the invention comprises one or more amino acid residues N-terminus leading from the "$Z^1Z^2SL$" motif, e.g. to form a sequence $XZ^1Z^2SL$ (SEQ ID NO: 36), $XXZ^1Z^2SL$ (SEQ ID NO: 37), $XXXZ^1Z^2SL$ (SEQ ID NO: 38), $XXXXZ^1Z^2SL$ (SEQ ID NO: 39), $XXXXXZ^1Z^2SL$ (SEQ ID NO: 40), $XXXXXXZ^1Z^2SL$ (SEQ ID NO: 41), $XXXXXXXZ^1Z^2SL$ (SEQ ID NO: 42) or $XXXXXXXXZ^1Z^2SL$ (SEQ ID NO: 43). Most preferably, the oligopeptide of the invention comprises the sequence $RXXXXXXXZ^1Z^2SL$ (SEQ ID NO: 7). For example, the sequences RXXXXXXXADSL (SEQ ID NO: 44), RXXXXXXXAHSL (SEQ ID NO: 45), RXXXXXXXDHSL (SEQ ID NO: 46) and RXXXXXXXDDSL (SEQ ID NO: 47) are present in preferred embodiments of the invention.

The forgoing considerations are not to be construed as implying any maximum length nor any limit on the extent, towards the C-terminus or N-terminus, of the oligopeptide of the invention, which could be more than 17 amino acids in length (e.g. 20-aa or up to 30-aa). The oligopeptide of the invention may have amino acid residues that extend further to the N-terminus than position 1 discussed above (i.e. "position 0", "position −1", etc, using the above numbering convention) and the oligopeptide of the invention may have amino acid residues that extend further to the C-terminus than position 17 discussed above (i.e. "position 18", etc, using the above numbering convention).

The oligopeptide of the invention may be referred to as an oligopeptide antigen.

Oligopeptides are defined herein as molecules comprising between 2 to 30 amino acid residues covalently linked together. An oligopeptide of the invention may have 'up to' (i.e. a number equal to or less than) 5 amino acid residues, 6 amino acid residues, 7 amino acid residues, 8 amino acid residues, 9 amino acid residues, 10 amino acid residues, 11 amino acid residues, 12 amino acid residues, 13 amino acid residues, 14 amino acid residues, 15 amino acid residues, 16 amino acid residues, 17 amino acid residues, 18 amino acid residues, 19 amino acid residues, 20 amino acid residues, 21 amino acid residues, 22 amino acid residues, 23 amino acid residues, 24 amino acid residues, 25 amino acid residues, 26 amino acid residues, 27 amino acid residues, 28 amino acid residues, 29 amino acid residues or 30 amino acid residues. For example, an oligopeptide that has 'up to 12 amino acids' may contain 4, 5, 6, 7, 8, 9, 10, 11 or 12 amino acids, but not more. Nevertheless, the oligopeptide of the invention may also include other (non-peptide) chemical or physical moieties.

In some embodiments, an oligopeptide of the invention may have exactly (i.e. a number equal to, but not more than) 4 amino acid residues, 5 amino acid residues, 6 amino acid residues, 7 amino acid residues, 8 amino acid residues, 9 amino acid residues, 10 amino acid residues, 11 amino acid residues, 12 amino acid residues, 13 amino acid residues, 14 amino acid residues, 15 amino acid residues, 16 amino acid residues, 17 amino acid residues, 18 amino acid residues, 19 amino acid residues, 20 amino acid residues, 21 amino acid residues, 22 amino acid residues, 23 amino acid residues, 24 amino acid residues, 25 amino acid residues, 26 amino acid residues, 27 amino acid residues, 28 amino acid residues, 29 amino acid residues or 30 amino acid residues. For example, an oligopeptide that has 12 amino acids contains 12 amino acids, not more. Nevertheless, the oligopeptide of the invention may also include other (non-peptide) chemical or physical moieties. The oligopeptide of the invention may have no more than 20 amino acids, no more than 30 amino acid residues, no more than 40 amino acid residues or no more than 50 amino acid residues. In some embodiments of the invention, the oligopeptide is defined as having a number of amino acids that takes a value of any two numbers recited above or any value in between.

Oligopeptide antigens are oligopeptide molecules that are capable of inducing an immune response, when recognised by an immune cell in the context of appropriate costimulatory signals. An oligopeptide antigen may bind to a B-cell receptor and/or an antibody and/or a T-cell receptor.

Amino acid residues denoted "X" represent any natural or unnatural amino acid residue.

The oligopeptide of the invention may be provided as part of a composition, for example a pharmaceutical composition suitable for administration to a patient. Compositions of the invention may comprise a pharmaceutically acceptable excipient, a variety of which are known in the art and need not be discussed in detail herein. A pharmaceutical composition can comprise a multimeric polypeptide of the present disclosure, and a pharmaceutically acceptable excipient. In some cases, a subject pharmaceutical composition will be suitable for administration to a subject, e.g., will be sterile. For example, in some embodiments, a subject pharmaceutical composition will be suitable for administration to a human subject, e.g., where the composition is sterile and is free of detectable pyrogens and/or other toxins. The compositions of the invention may comprise other components, such as pharmaceutical grades of mannitol, lactose, starch, magnesium stearate, sodium saccharin, talcum, cellulose, glucose, sucrose, magnesium, carbonate, and the like. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate, hydrochloride, sulfate salts, solvates (e.g., mixed ionic salts, water, organics), hydrates (e.g., water), and the like.

EXAMPLES

The following examples are set forth so as to provide those of ordinary skill in the art with a complete disclosure and description of how to practise the invention, and are not intended to limit the scope of the invention.

Example 1

Sequence Alignment of the Oligopeptides of the Invention

The amino acid sequences of exemplary oligopeptides of the invention are set forth here:

```
"S"  RLTLSPEQAHSLILQHL                    (SEQ ID NO: 18)

"H"    MPRTQENAHSLERCWL                   (SEQ ID NO: 19)

"P"  RGSRGQHQAHSLERVCH                    (SEQ ID NO: 20)

"F"  RVPGCAHHADSLYTYPV                    (SEQ ID NO: 21)

"E"  RHSDEHHHDDSLPHPQQ                    (SEQ ID NO: 22)

"A"  RDSANIYHADSLKGRFT                    (SEQ ID NO: 23)

RLGTHVLEAHSLDKVSH                    (SEQ ID NO: 24)

RMSTPNPHADSL                         (SEQ ID NO: 25)

SSPEHRLAHSLERDYG                    (SEQ ID NO: 26)

RLTLSPEQAHSL                         (SEQ ID NO: 27)

RGSRGQHQAHSL                         (SEQ ID NO: 28)

RVPGCAHHADSL                         (SEQ ID NO: 29)

RHSDEHHHDDSL                         (SEQ ID NO: 30)

RDSANIYHADSL                         (SEQ ID NO: 31)

RLGTHVLEAHSL                         (SEQ ID NO: 32)
```

The sequences of SEQ ID NOs: 18-26 are also shown in FIG. 13.

Example 2

Antibody Detection Assays of the Invention

Materials and Methods
ELISA Assay

Six exemplary oligopeptides of the invention (each 17 amino-acids long, with biotinylated N-terminus) were used to prepare ELISA assays for studying antibody levels in patient samples. The oligopeptides were synthesised by K J Ross-Petersen ApS (Copenhagen, Denmark) and provided in lyophilized form. General serum diluent was purchased from Immunochemistry Technologies LLC (Minnesota, USA). Streptavidin coated 96-Well microplates were purchased from Eagle Biosciences (New Hampshire, USA) and the oligopeptides were applied to individual wells of the streptavidin plates as described below.

Sample preparation: Following obtaining informed consent, a 5 ml venous blood sample was withdrawn from each individual participating in this study. Samples were centrifuged for 10 minutes at 3000 RPM. Serum was then transferred into a clean plastic vial and the remainder was discarded. Serum was then diluted in general serum diluent (200 µl/mL), labelled accordingly and stored at −20° C. Serum samples were diluted into 1:2 ratio by mixing 250 µL of serum with 250 µL General Serum Diluent. The oligopeptide antigens of the invention were diluted in saline (2000 ng/mL).

ELISA protocol: Typical ELISA protocol was followed for quantifying antibodies present in serum. After equilibrating microplate to room temperature, 100 µl of the appropriately diluted biotinylated oligopeptide antigen of the invention to each well of the 96-well microplate. The plate was incubated for 50 minutes in static condition at room temperature before shaking it for 10 minutes at 250 RPM. Then, well contents were emptied and 300 µl of Wash Buffer was used to wash each well four times. Subsequently, 100 µl of the diluted serum sample was added into each well. The plate was again incubated for 50 minutes in static condition at room temperature before shaking it for 10 minutes at 250 RPM. Well contents were emptied and 300 µl of Wash Buffer was used to wash each well four times. Then, 100 µl of HRP conjugate was added into each well with the final ratio of 1 in 8000 µl. Following this, the plate was incubated in static condition at room temperature. After an hour, well contents were emptied and 300 µl of Wash Buffer was used to wash each well four times. Subsequently, 50 µl of TMB substrate was added to each well and incubated for 15 minutes at room temperature prior addition of 100 µl of 1N HCL. The plate was shaken for 5 seconds at 250 RPM and absorbance was measured using plate reader at wavelength 450 nm and 630 nm filter. Elisys Uno fully automated ELISA analyser (HUMAN company, Wiesbaden, Germany) was used to read the measurements. Phosphate buffered saline (PBS), used as wash buffer, was purchased from Sigma-Aldrich (USA).

Magnetic ELISA Assay

Magnetic ELISA assays follow a similar protocol to the standard ELISA described above and elsewhere herein. In common with the standard ELISA assays of the invention, the magnetic ELISA assays of the invention utilize an oligopeptide of the invention to bind the antibody. The main difference in the present magnetic ELISA protocol is that 100 µl of each oligopeptide antigen of the invention was incubated with 200 µl of streptavidin-coupled Dynabeads for 1 hour at room temperature. These magnetic beads were purchased from Thermofisher Scientific (Massachusetts, USA). Each well of a clear 96-well microplate was then incubated with 200 µl of this mixture for 50 minutes in static condition at room temperature before being shaken for 10 minutes at 250 RPM. Then, well contents were emptied and 300 µl Wash Buffer was used to wash each well four times. Subsequently, 100 µl of the diluted serum sample was added into each well and the remainder of the protocol was as described for the standard ELISA assay.

The skilled person will appreciate that other methods can also be used to detect the levels of antibodies. These methods include chemiluminescence, protein array, fluorescence in situ hybridization (FISH) and western blot. Methods for these assays are well known in the art, e.g. the Molecular Cloning manual by Green and Sambrook, $4^{th}$ edition.

Results
ELISA Assays

Antibody levels were determined in the blood samples from male and female subjects using the herein described methods for performing ELISA assays.

FIG. 1 compares the antibody levels of healthy female patients (HF), female patients with MS (FMS), healthy male patients (HM), male patients with MS (MMS). In healthy subjects, the levels of antibody specific for the oligopeptides of the invention is higher in female than male individuals.

For both male and female subjects, the levels of antibody specific for the oligopeptides of the invention is higher in healthy subjects compared to MS subjects. This observation can be explained as FSH antibody in MS patients has been already taken and eliminated from the body because of the disease nature compared to FSH antibody of healthy subjects that has not been used or eliminated from serum. Significant differences were observed in the levels of antibody that bind the exemplary oligopeptides of the invention.

Figure 2:
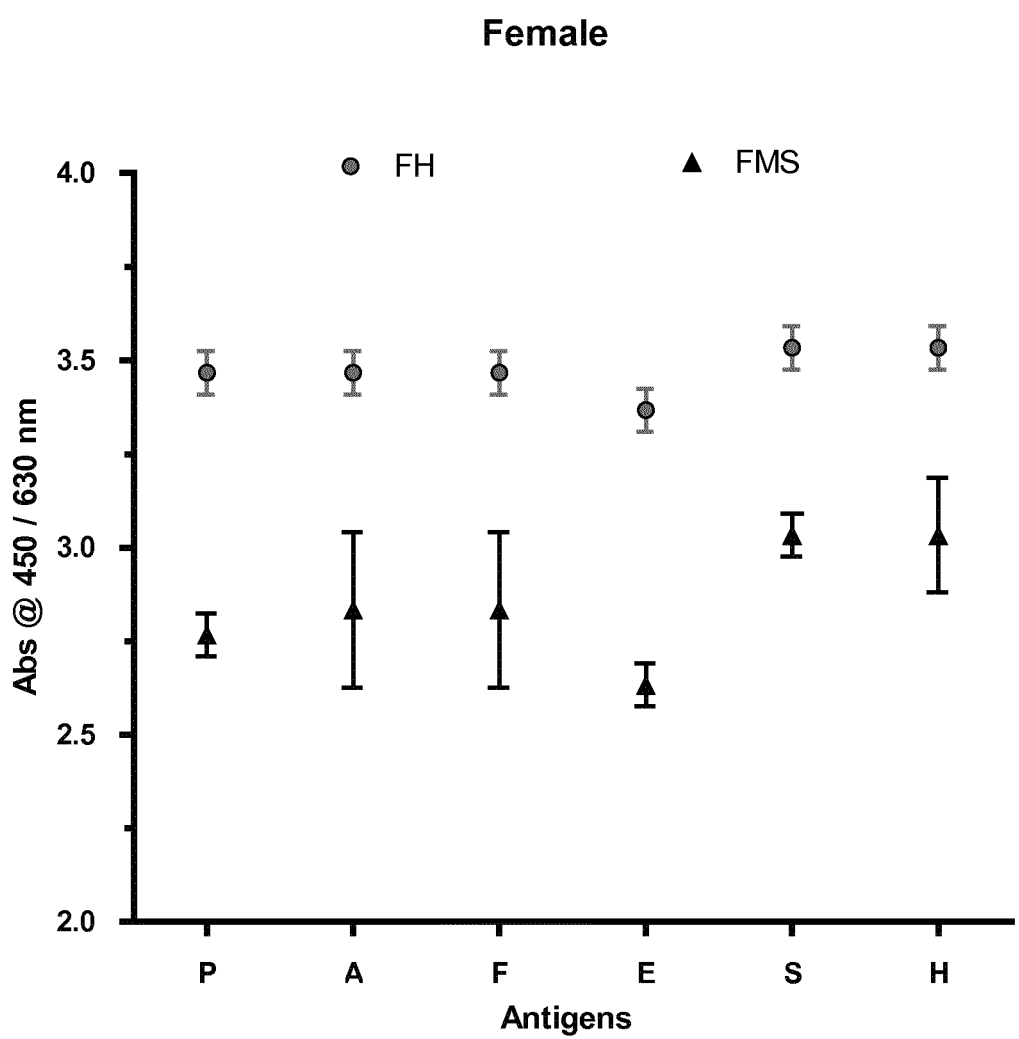
FIG. 2. Diagnostic blood test—ELISA assay on female samples at pH 7.4. Levels of antibody in healthy female patients (HF) and female patients with MS (FMS) that bind to the indicated exemplary oligopeptides of the invention.

FIG. 2 shows that differences are observed between healthy female patients (HF) and female patients with MS (FMS) in the levels of antibody that bind to the exemplary oligopeptides of the invention. These differences were significant for each exemplary oligopeptide besides H and S. Oligopeptides E and P are the best candidates for use in diagnosis of MS in female subjects.

Figure 3:
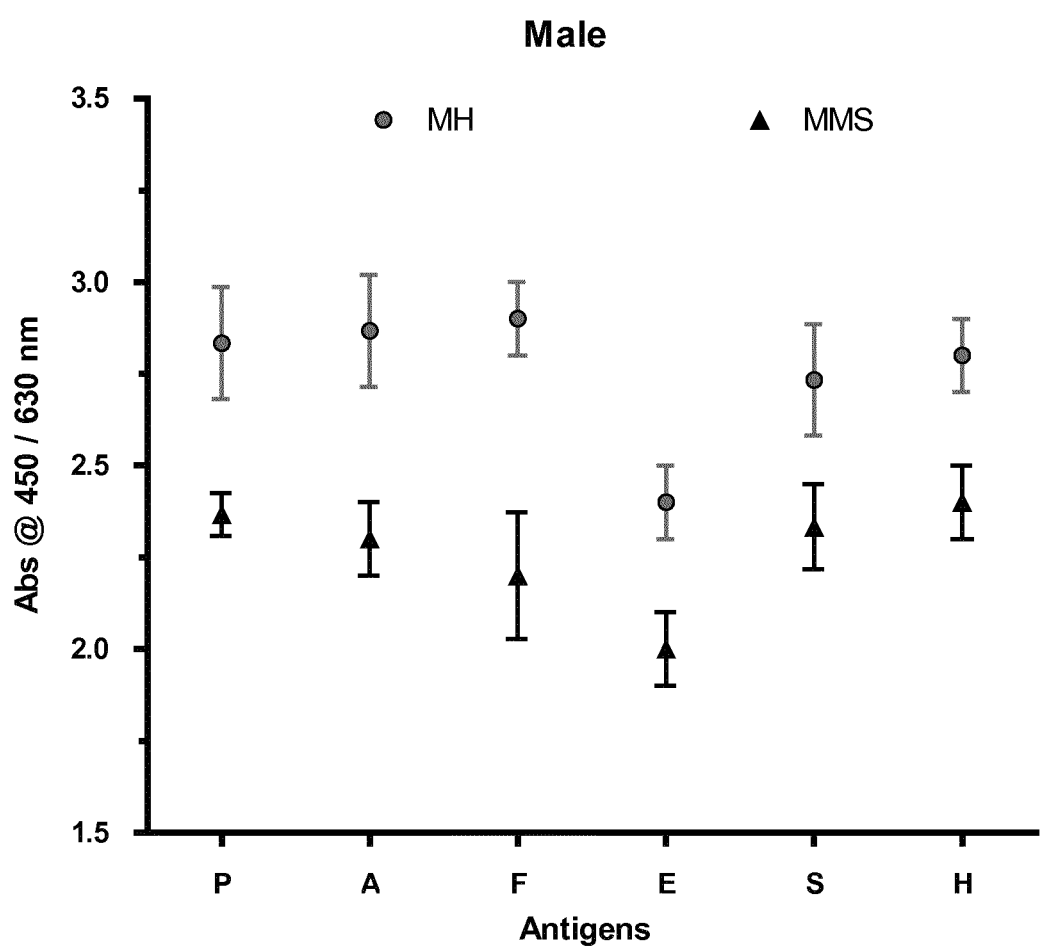
FIG. 3. Diagnostic blood test—ELISA assay on male samples at pH 7.4. Levels of antibody in healthy male patients (HM) and male patients with MS (MMS) that bind to the indicated exemplary oligopeptides of the invention.

FIG. 3 shows that differences are observed between healthy male patients (HM) and male patients with MS (MMS) in the levels of antibody that bind to the exemplary oligopeptides of the invention. Oligopeptides A and F are the best candidates for use in diagnosis of MS in male subjects.

Figure 4:
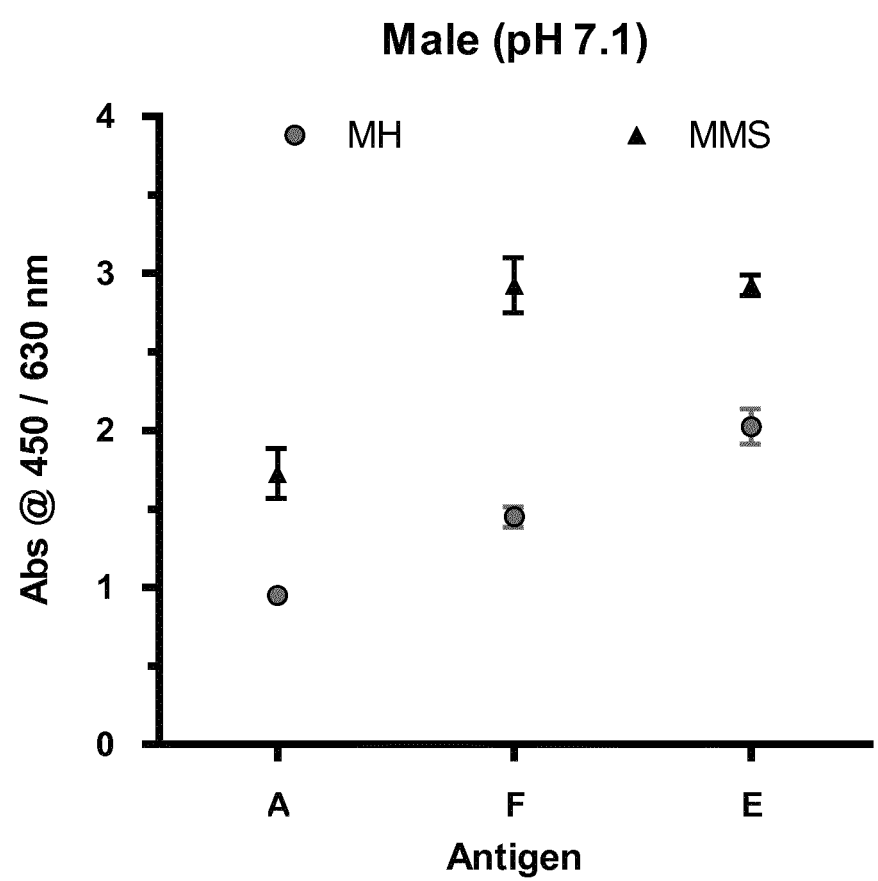
FIG. 4. Diagnostic blood test—ELISA assay on male samples at pH 7.1. Levels of antibody in healthy male patients (HM) and male patients with MS (MMS) that bind to the indicated exemplary oligopeptides of the invention.

FIG. 4 shows that by changing the pH into a more acidic environment (pH=7.1) compared to normal body pH=7.4, the titer of MS specific antibodies approximately remained the same (about 10% change at most) whilst the binding level of healthy antibodies in the serum decreases significantly.

The ELISA results showed that MS can be successfully detected with an accuracy of 85% in female and 95% in male patients from healthy individuals in the presences of 2 (or more) oligopeptide antigens of the invention.

Example 3

Animal Models of Demyelinating Disease

Materials and Methods

Male (n=16) and female (n=16) C57BL/6 mice, weighing between 16-18 g, were purchased from Royan institute (Tehran, Iran). MS induction study started when mice reached 6-8 weeks of age. Similar investigations were carried chick and guinea pig (data not shown). All procedures were performed aseptically and under supervision of Gandhi Hospital medical ethics committee (Tehran, Iran). Freund's complete adjuvant and Pertussis toxin purchased from Sigma-Aldrich (Dorset, UK).

Administration of antigen and adjuvant in combination with Pertussis toxin

At day 1 and day 2, 250 µg of antigen (oligopeptides of the invention) diluted in 150 µl of saline combined with 150 µl of adjuvant was injected intra-dermally into alcohol wiped back of each mouse. Following the injection of antigens, 400 ng Pertussis toxin diluted in 300 µl distilled water was injected intraperitoneally. Two control groups received either 150 µl distilled water in 150 µl of adjuvant or 400 ng Pertussis toxin diluted in 300 µl distilled water. The animals were kept in standard housing condition with appropriate temperature and humidity as well as adequate supplies of food and fresh water.

Administration of Antigen and Adjuvant without Pertussis Toxin

C57BL/6 mice were injected with adjuvant and antigens (oligopeptides of the invention) at day 0 and 5. Control group received the injection of only adjuvant in distilled water.

Histological Analysis of Plaque Formation

After scarifying mice by anaesthesia overdose at day 15 of injection, their brain was dissected out and fixed in 10% Formalin for histological analysis. The fixed samples were subsequently cut horizontally and processed to produce 5-micron thin paraffin sections, which then were stained with Haematoxylin and eosin (H&E), Glial fibrillary acidic protein (GFAP), CD-68 and Luxol fast blue (LFB). Various sections of the brain were then analyzed and imaged using a bright-field microscope (Optika B-383PL, Bergamo, Italy). Grade of plaque formation was defined as number of plaques measured in mid brain section as follow:

| Grade | Plaque No. |
|---|---|
| 1 | 0-3 |
| 2 | 3-6 |
| 3 | 6-9 |
| 4 | 9-12 |
| 5 | 12-15 |
| 6 | 15-18 |
| 7 | 18-21 |
| 8 | 21-24 |
| 9 | 24-27 |
| 10 | 27-30 |

Analysis of Disease Models on Muscular Function

The effect of injected oligopeptide antigens of the invention on muscular function was tested by measuring animal fall time from inverted cage and ring. These tests follow the format of commonly used functional muscle evaluation tests in mice that use "wire hanging" behavioral tests wherein latency to fall after being suspended from a substrate is quantified to give a measure of muscular function.

Results & Discussion

Disease Induction with Antigen and Adjuvant in Combination with Pertussis Toxin

Figure 5:
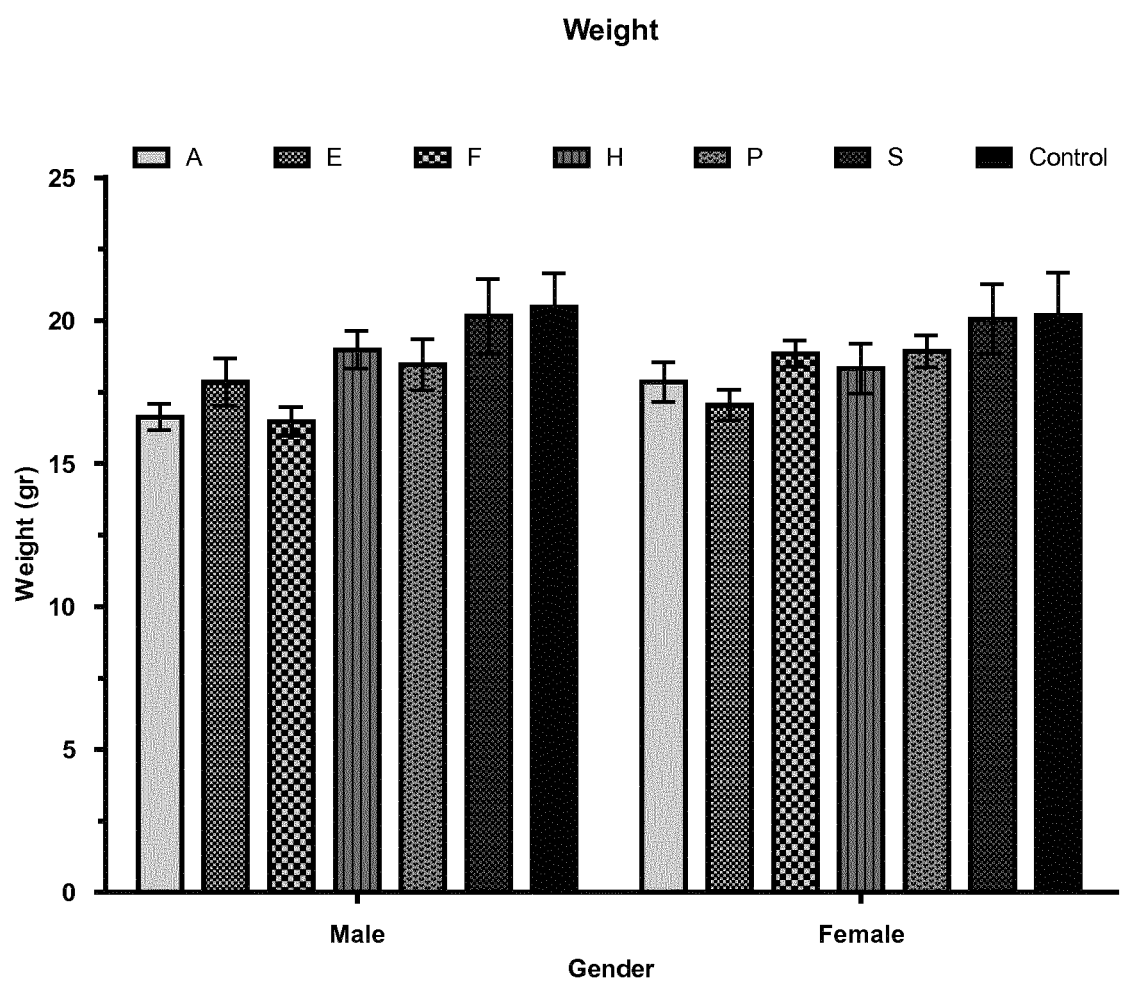
FIG. 5. The effect on animal weight of disease induction with antigen and adjuvant in combination with Pertussis toxin. Significant weight loss is observed, compared to the control group, in the disease-induced mice, using each indicated oligopeptide antigen of the invention except for antigen S, where there was a non-significant weight loss.

Significant weight loss, compared to control group, was observed in the MS induced mice that were treated with Pertussis toxin and adjuvant in combination with each one of the exemplified oligopeptide antigens of the invention, except antigen S (FIG. 5).

Histology—Antigen & Adjuvant in Combination with Pertussis Toxin

Injection of pertussis damages the meninges of the brain, resulting in the influx of T cells and antibodies into CNS. This finding is replicated when adjuvant and administration of oligopeptide antigens of the invention is coupled with administration of Pertussis toxin, confirmed by microscopically visualization of plaques in the mice injected with pertussis versus those injected with distilled water and adjuvant (data not shown). (It is known that plaques are found in control group in the Experimental autoimmune encephalomyelitis (EAE) studies, where the severity of the plaque formation is Grade 3 from the range of Grade 1 to 10 (6,8).)

Histology—Antigen & Adjuvant without Pertussis Toxin

Figure 9:
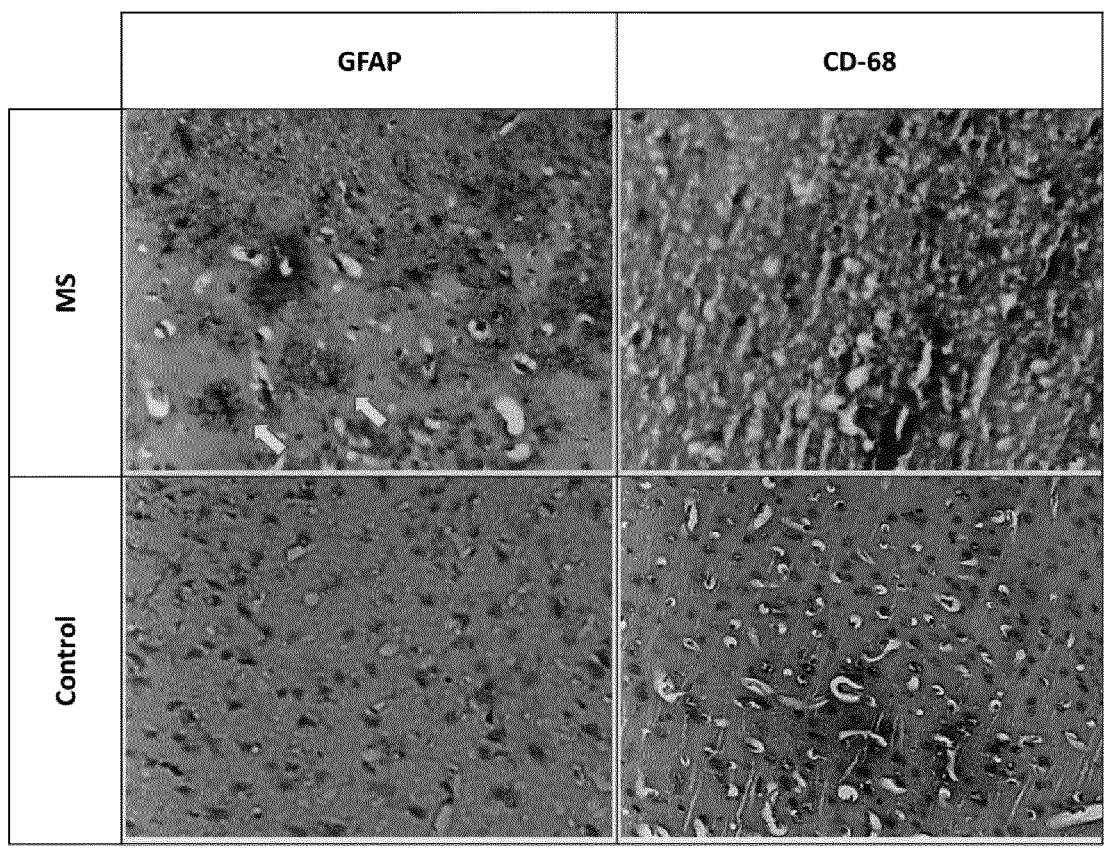
FIG. 9. Histology of brain samples from control animals and from disease model animals administered with antigen & adjuvant without Pertussis. Brain samples were stained for GFAP (left column) and CD-68 (right column). Disease model animals labeled "MS" (upper row).
Figure 10:
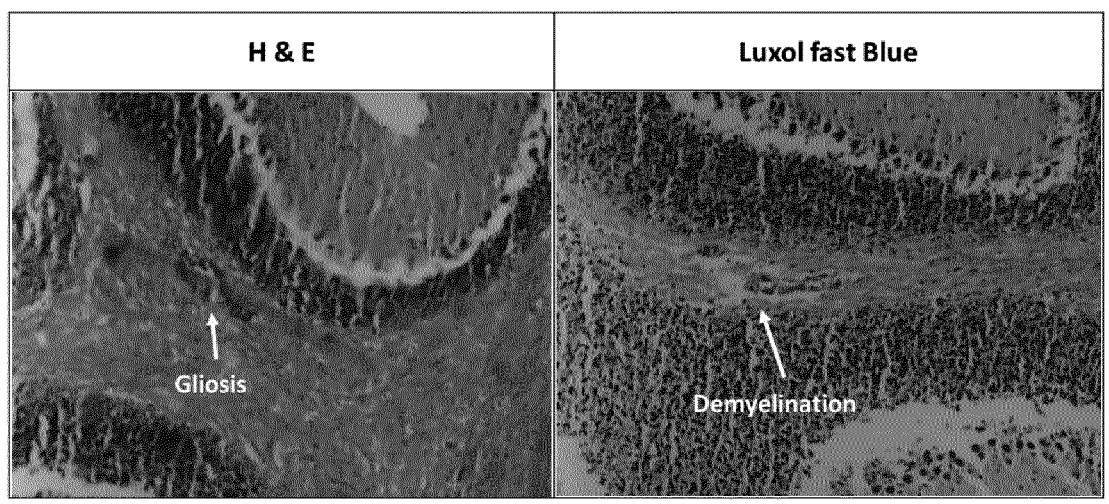
FIG. 10. Histology of brain samples from disease model animals administered with antigen & adjuvant without Pertussis. Brain samples were stained for H&E (left panel) and Luxol fast blue (right panel).
Figure 11:
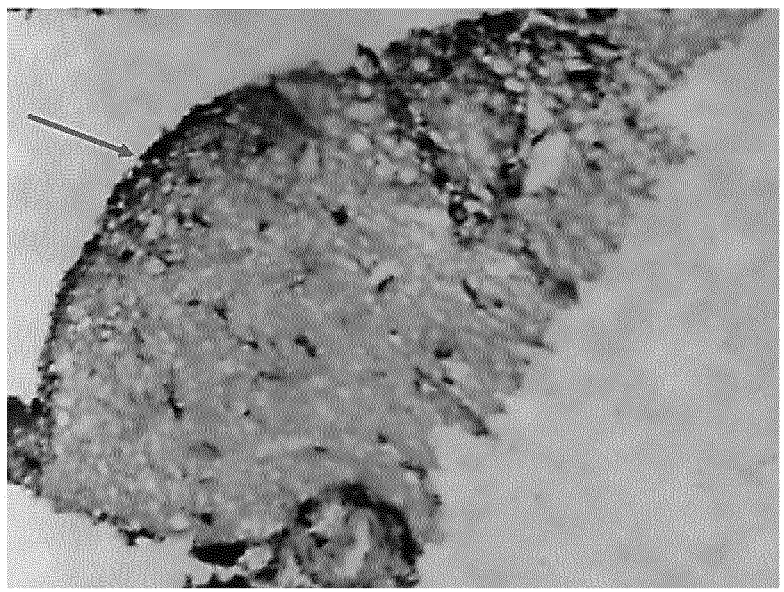
FIG. 11. Histology of brain samples from disease model animals administered with antigen & adjuvant without Pertussis. Brain sample was stained for GFAP. GFAP staining of hypophysis of mouse shows reactivation of astrocytes.

Plaque formation in animals administered with the exemplified oligopeptide antigens of the invention, and with adjuvant but without Pertussis, was observed by staining fixed brain sections with GFAP (for gliosis) and CD-68 (for inflammation) (FIG. 9) and H&E, Luxol fast blue (for demyelination) (FIG. 10)). Positive GFAP staining of hypophysis of MS positive mouse is shown in FIG. 11. This process does not impose any physical or chemical damage of the blood-brain barrier (BBB), as it mimics a naturally developing MS condition. Histology images are representative of all slides obtained from subject animals.

Figure 12:
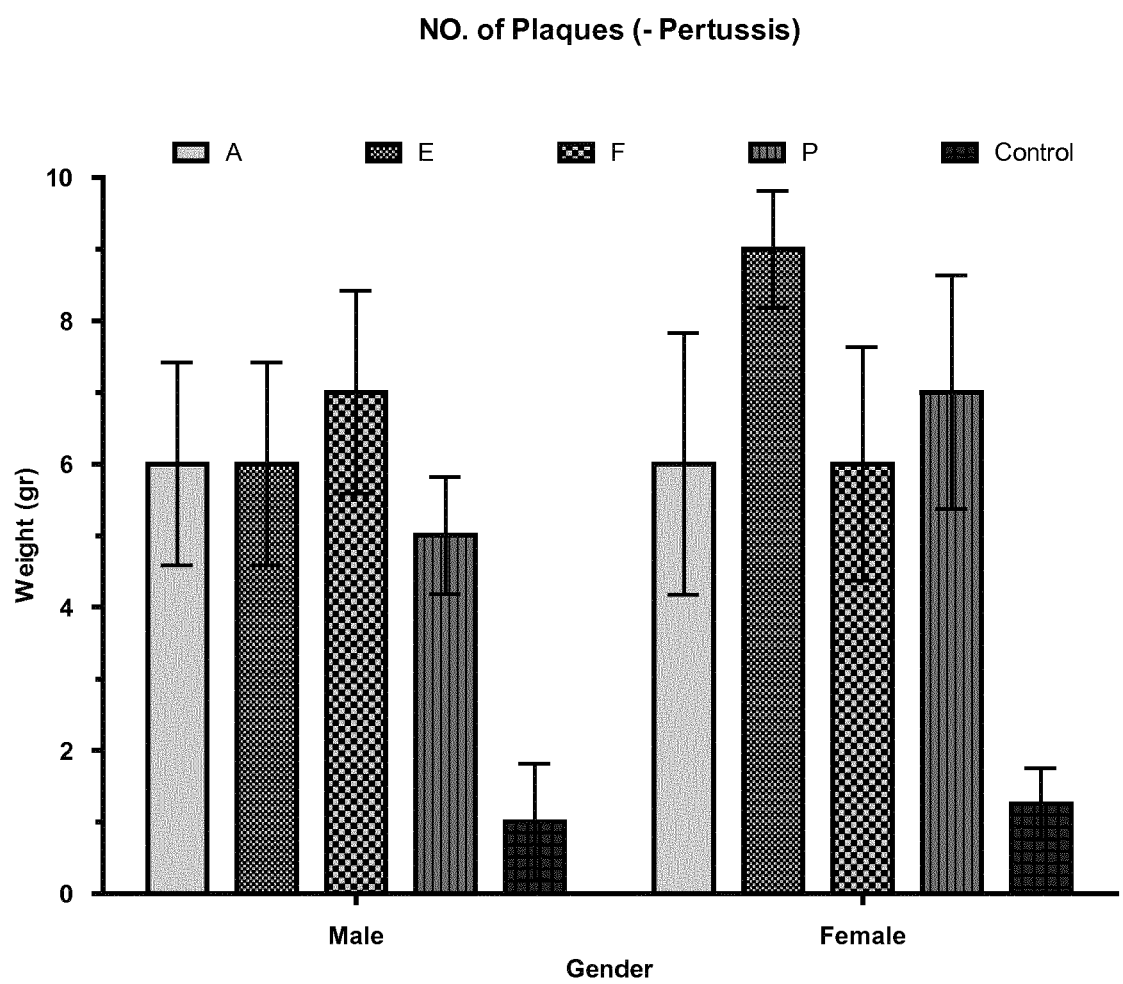
FIG. 12. Grade of plaques in animals administered with antigen & adjuvant without pertussis. Grade of the formed plaques using each indicated exemplary oligopeptide antigen of the invention was significantly higher than that of the control animals.

FIG. 12 shows the grade of plaque formation in each animal group administered with the exemplified oligopeptide antigens of the invention together with adjuvant but without Pertussis. Oligopeptide antigen E led to formation of plaque at the highest grade (9) in female mice whilst grade of plaque formation is male mice was at highest (7) in group injected with oligopeptide antigen F.

Effect of Disease Models on Muscular Function

Figure 6:
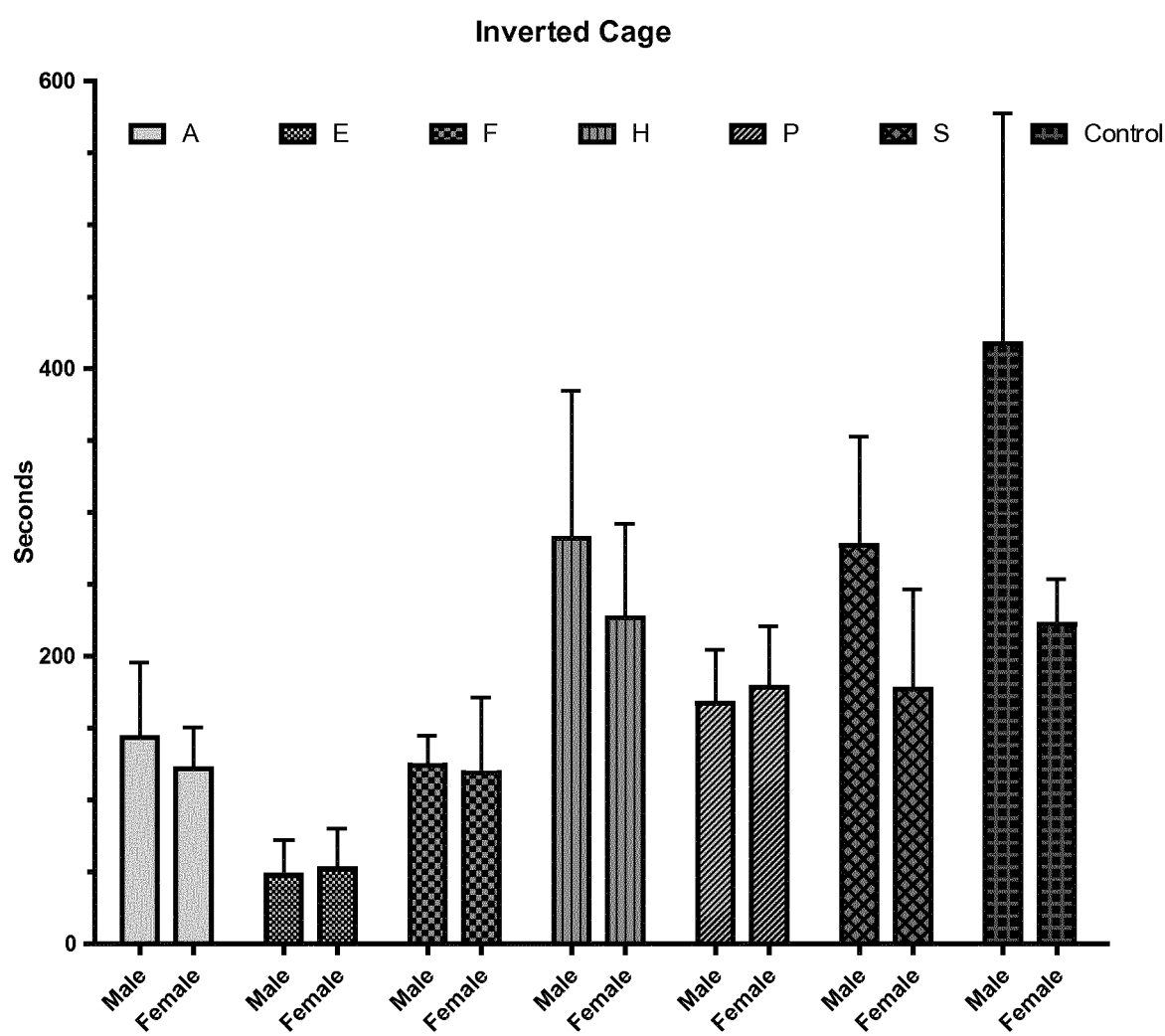
FIG. 6. Inverted cage holding time of animals injected with the combination of antigen, adjuvant and pertussis. Decreased falling time indicates decrease in their muscle strength, relative to control animals, in disease induced animals administered with each indicated oligopeptide antigen of the invention.
Figure 7:
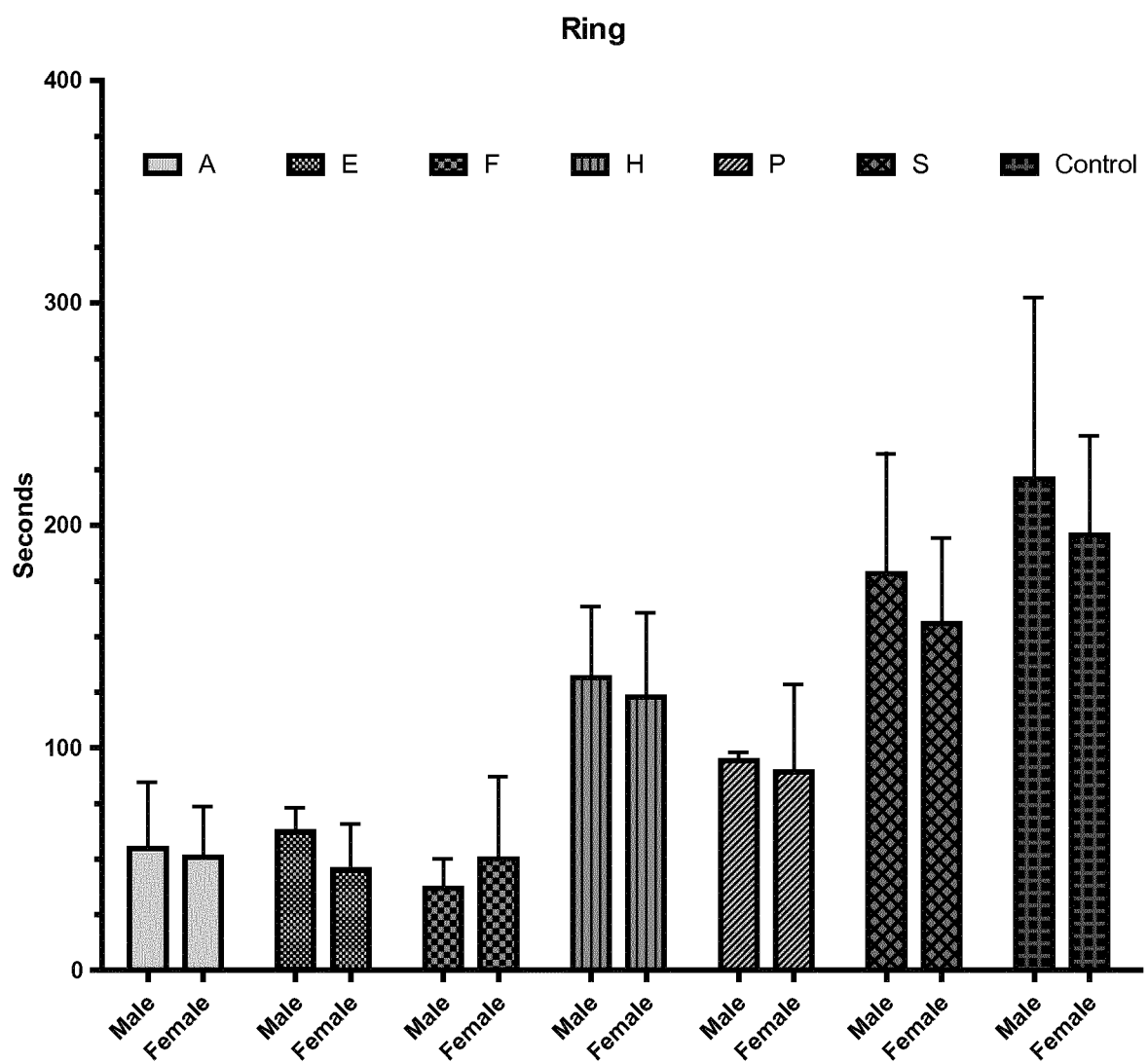
FIG. 7. Ring holding time of animals injected with the combination of antigen, adjuvant and pertussis. Decreased falling time indicates decrease in their muscle strength, relative to control animals, in disease induced animals administered with each indicated oligopeptide antigen of the invention.
Figure 8:
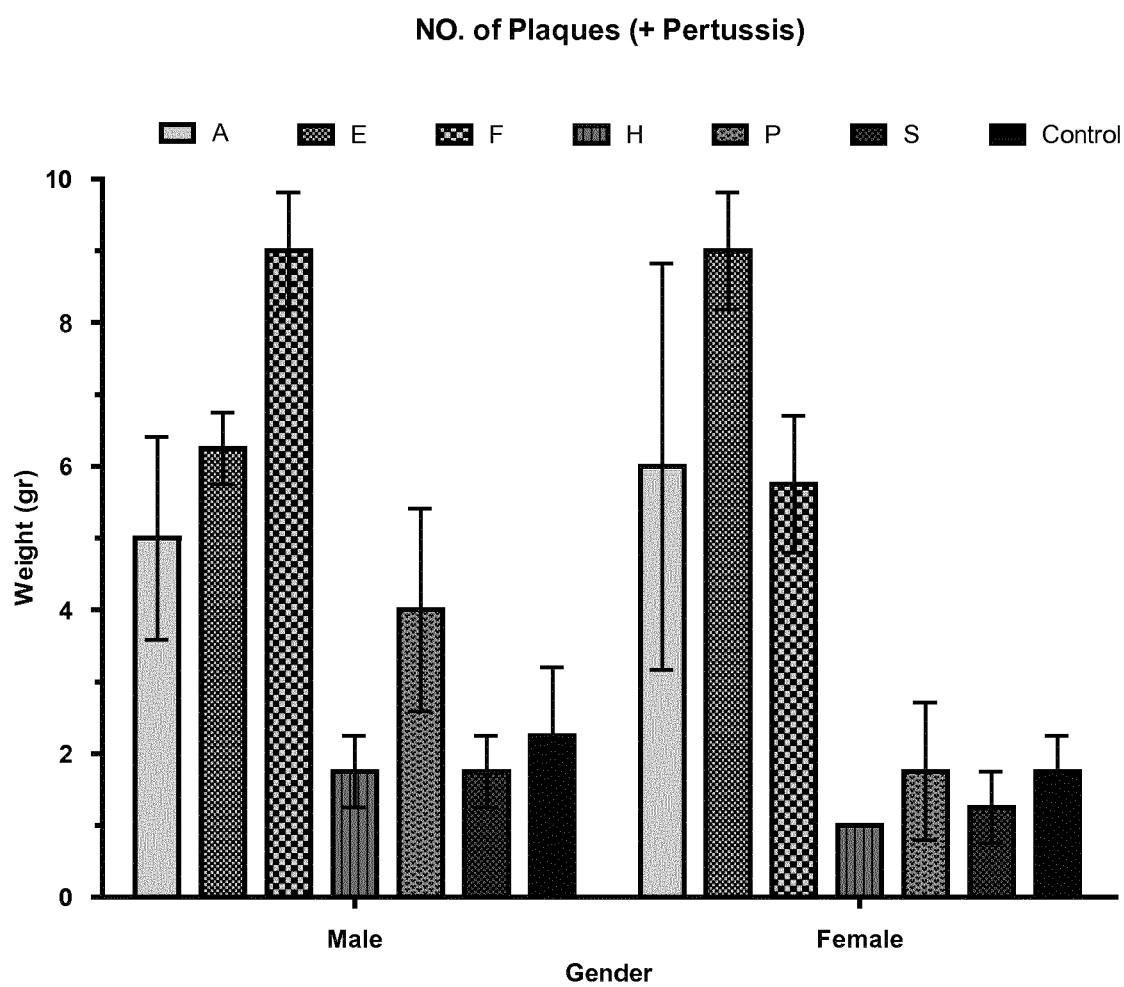
FIG. 8. Grade of plaques in animals administered with the combination of antigen, adjuvant and pertussis. Grade of the plaques formed using oligopeptide antigens A, E and F was significantly higher than that of the control animals. Less plaque was found in the mice injected with oligopeptide antigens H and S compared to the control group.

FIG. 6 and FIG. 7 show the effect of injected oligopeptide antigens of the invention on muscular function. Muscular function was tested by timing animal fall time from inverted cage and ring. These tests provide a measure of the muscular function of the animal subject. In both tests, the disease model mice of the invention showed significant decrease in their muscle strength compared to control groups. The falling time was considerably dependent on the affected limb (forelimb, hindlimb or both). This phenomena is similar to that in MS patients where the formation of plaques in brain causes severe fatigue.

Oligopeptide antigen F induced the most pronounced muscle weakness in male and oligopeptide antigen E caused the most pronounced muscle weakness in female mice. The severity in animals injected with oligopeptide antigen A was less than those injected with oligopeptide antigen P. Both had considerably less effect than oligopeptide antigens E and F.

The inventors conclude that oligopeptide antigens H and S could act as antagonists, in a similar manner to interferon-beta, by preventing the binding of agonistic antigens to either specific antibody or T cell. Therefore neither of these two oligopeptide antigens of the invention were taken forward for the animal study into disease induction without pertussis.

Example 4

Therapeutic Approaches

Background

In a 'normal' immune system, tolerance to self-antigens and other innocuous, non-infectious environmental antigens is achieved by silencing the immune response in an antigen-specific manner. This is done centrally and/or in the periphery, by a number of mechanisms such as clonal deletion or desensitization of autoreactive lymphocytes, or by immunological suppression by regulatory T cells (Treg cells) specific to the innocuous or self-antigen.

Autoimmune reactions can result when tolerance to self-antigens is broken. Demyelinating diseases typically have an autoimmune component. For example, in MS, lymphocytes and leukocytes are found at the site of the lesion and are thought to play an important role in the inflammation associated with MS. While the identity of all the self-antigens that may be a target of the autoimmune reactions of demyelinating diseases is unknown, research in this area is continuing. For instance the amino acid sequence "ENPVVHFFKNIVTPR" has been identified by many studies and differential splicing or the expression of embryonic, rather than mature variants of myelin autoantigens have been associated with strain-specific susceptibility to EAE is thought to play a role in the pathogenesis of multiple sclerosis in humans (19).

Glatiramer acetate (also known as Copolymer 1, Cop-1, or Copaxone) is a random polymer of four amino acids found in myelin basic protein. This agent is currently used to treat multiple sclerosis, where it is administered as an immunomodulator drug. Patients treated with Copaxone suffer about 30% fewer relapses than patients taking placebo (20). It is a self-injection drug with the dosage of 20 mg per day or 40 mg per week (three times per week).

Establishment of Tolerance

Immunological tolerance manifests as a state of unresponsiveness to a particular antigen, which is primarily established in T- and B-lymphocytes (19). This is achieved both 'centrally' and 'peripherally'. Central tolerance is achieved in the central lymphoid organs of the bone marrow and thymus, during which lymphocytes that react strongly to particular antigens are deleted, or altered so as not to respond aggressively to that antigen. Peripheral mechanisms for establishing tolerance to a particular antigen include the induction of anergy in lymphocytes that were responsive to that particular antigen and the establishment of antigen specific Treg cells (19).

The immune system has no direct way to determine whether a particular molecule is exogenous or is a self-antigen (originating from the host), thus the context in which the immune system encounters an antigen shapes the response, and subsequent responses, to that antigen. It is well known that the administration of large doses of antigens in the absence of costimulatory signals can lead to specific tolerance to that antigen and the route of administration can also increase the tolerogenic effect of the antigen, with intravenous, oral, intranasal or aerosol mediated routes particularly preferred (19). Peptide antigens can also act as decoy ligands for autoimmune antibodies and/or as T-cell receptor antagonists.

Preliminary experiments showed that oligopeptides of the invention can act as antagonists to MS antigens (such as Interferon and Helicobacter pylori). Oligopeptide antigen of the invention denoted "E" is a major inducer of MS in females whereas Oligopeptide antigen of the invention denoted "F" is a major inducer of MS in males.

Administration via injection or inhalation can lead to elimination of MS antibodies present in the blood; whilst taking the drug orally can eliminate MS by changing IgG to IgA in the intestine. Existing oral medications such as fingolimod are currently in use for the latter method but being non-specific, they suppress the whole immune system.

As described herein, the oligopeptides of the present invention may be administered to subjects suffering from disease of the myelin sheath, including demyelinating diseases such as MS. Administration in the absence of adjuvants or other immunostimulators induces tolerance. In one embodiment, the oligopeptide of the invention is administered to a human MS patient by intravenous injection at a dosage of 20 mg per day.

Example 5

Study of Disease Induction and Treatment in Chicks

Following successful identification of the specific antigens responsible for demyelination in MS, we successfully induced MS in 5 animals with PLP structure similar to human PLP, using these antigens combined with adjuvant. In this situation, T cells become active and the immune system starts to produce antibodies against our identified antigens. Our proposed treatment strategy is based on elimination of these produced antibodies.

As a preliminary examination of our proposed treatment method, we induced MS in chicks by injecting antigens P, F, E and A (corresponding to SEQ ID NOs: 20, 21, 22 and 23) combined with pertussis and adjuvant. The dosage was 1 mg antigen per 70 g body weight. The main reason we chose this animal was to be able to easily visualize the walking impairment as they are bipedal like humans (compared to quadrupedal rodents). Initial symptoms were seen 12 days after antigen injection. Significant weight loss and lack of balance were visible in MS samples compared to controls.

In order to treat the MS chicks, antigens P, F, E and A were injected at high dose (3 mg antigen per 70 g body weight) to animals three times (at days 20, 23 and 26 after initial injection) without co-administration of adjuvant or pertussis toxin.

Weight gain and improved balance was observed at 7 days following the last treatment injection (day 33 after disease induction). At 19 days following the last treatment injection (day 45 after disease induction), no significant difference between the treated MS chicks and controls chicks was observed.

Example 6

Conclusions

The inventors have identified MS specific oligopeptide antigens that are present in known factors related to MS, such as Helicobacter pylori, Human herpesvirus 4 and HCG. The structure of antigens related to MS have a 'R' amino acid at position 1 and ADSL or AHSL or DDSL at position 9, 10, 11 and 12 related to 'R'. Among the claimed MS antigen sequences, antigens P and E can be specifically used for diagnosis of MS in female patients; whereas antigens A and F can be used for male patients.

Antigens with structure such as H and S with amino acid 'H' instead of 'D' can act as antagonists and have increased therapeutic potential for MS treatment. Presence of amino acids E and R at positions 13 and 14 related to 'R can be beneficial factor Differences exist between female and male patients both in MS severity and in the prevalence and concentration of antibodies specific to the oligopeptide antigens of the invention.

The inventors have successfully developed MS animal model for the first time without any damage to the BBB using Pertussis toxin or using myelin antigens commonly used co in EAE studies. The inventors concluded that increase in follicle stimulating hormone (FSH) binding antibody can lead to induction of MS. Both environmental and genetic factors can trigger this increase.

Paragraphs of the Disclosure

The following paragraphs define embodiments of this disclosure that are related to the present invention:

1. An oligopeptide comprising amino acid sequence "$Z^1Z^2SL$" (SEQ ID NO: 1), wherein
   $Z^1$ is "A" (alanine) or "D" (aspartic acid), and
   $Z^2$ is "D" (aspartic acid) or "H" (histidine).
2. The oligopeptide according to paragraph 1, wherein the amino acid sequence "$Z^1Z^2SL$" is "$AZ^2SL$" (SEQ ID NO: 2).
3. The oligopeptide according to paragraph 1, wherein the amino acid sequence "$Z^1Z^2SL$" is "$DZ^2SL$" (SEQ ID NO: 3).
4. The oligopeptide according to paragraph 2, wherein the amino acid sequence "$AZ^2SL$" is "ADSL" (SEQ ID NO: 4).
5. The oligopeptide according to paragraph 2, wherein the amino acid sequence "$AZ^2SL$" is "AHSL" (SEQ ID NO 5).
6. The oligopeptide according to any one of paragraphs 1-5, wherein the oligopeptide comprises amino acid sequence "RXXXXXXXZ$^1$Z$^2$SL" (SEQ ID NO: 7).
7. The oligopeptide according to any one of paragraphs 1-6, wherein the oligopeptide comprises amino acid sequence "HZ$^1$Z$^2$SL" (SEQ ID NO: 8).
8. The oligopeptide according to any one of paragraphs 1-6, wherein the oligopeptide comprises amino acid sequence "QZ$^1$Z$^2$SL" (SEQ ID NO: 9).
9. The oligopeptide according to any one of paragraphx 1-8, wherein the oligopeptide comprises amino acid sequence "Z$^1$Z$^2$SLE" (SEQ ID NO: 12).
10. The oligopeptide according to any one of paragraphs 1-9, wherein the oligopeptide comprises amino acid sequence "Z$^1$Z$^2$SLXR" (SEQ ID NO: 13).
11. The oligopeptide according to paragraph 10, wherein the oligopeptide comprises amino acid sequence "Z$^1$Z$^2$SLER" (SEQ ID NO: 34)
12. The oligopeptide according to any one of paragraphs 1-11, wherein the oligopeptide comprises amino acid sequence "SXXXXXZ$^1$Z$^2$SL" (SEQ ID NO: 14).
13. The oligopeptide according to any one of paragraphs 1-11, wherein the oligopeptide comprises amino acid sequence "PXXXXXZ$^1$Z$^2$SL" (SEQ ID NO: 15).
14. The oligopeptide according to any one of paragraphs 1-13, wherein the oligopeptide has 12-17 amino acids.
15. The oligopeptide according to paragraph 14, wherein the oligopeptide has 12 amino acids.
16. The oligopeptide according to paragraph 14, wherein the oligopeptide has 17 amino acids.
17. The oligopeptide according to any one of paragraphs 1-13 or 16, wherein the oligopeptide consists of amino acid sequence "RXXXXXXXZ$^1$Z$^2$SL" (SEQ ID NO: 17).
18. The oligopeptide according to paragraph 3, wherein the amino acid sequence "DZ$^2$SL" is "DDSL" (SEQ ID NO: 6).
19. The oligopeptide according to paragraph 1, wherein the amino acid sequence consists of a sequence which is selected from the group consisting of:

```
                                          (SEQ ID NO: 18)
RLTLSPEQAHSLILQHL, (SEQ ID NO: 19)
MPRTQENAHSLERCWL, (SEQ ID NO: 20)
RGSRGQHQAHSLERVCH, (SEQ ID NO: 21)
RVPGCAHHADSLYTYPV, (SEQ ID NO: 22)
RHSDEHHHDDSLPHPQQ, (SEQ ID NO: 23)
RDSANIYHADSLKGRFT, (SEQ ID NO: 24)
RLGTHVLEAHSLDKVSH,
```

```
                                        (SEQ ID NO: 25)
RMSTPNPHADSL,
and (SEQ ID NO: 26)
SSPEHRLAHSLERDYG.
```

20. The oligopeptide according to paragraph 1, wherein the amino acid sequence consists of a sequence which is selected from the group consisting of:

```
                                        (SEQ ID NO: 27)
RLTLSPEQAHSL, (SEQ ID NO: 28)
RGSRGQHQAHSL, (SEQ ID NO: 29)
RVPGCAHHADSL, (SEQ ID NO: 30)
RHSDEHHHDDSL, (SEQ ID NO: 31)
RDSANIYHADSL,
and (SEQ ID NO: 32)
RLGTHVLEAHSL.
```

21. A nucleic acid encoding the oligopeptide according to any one of paragraphs 1-20, wherein the nucleic acid is capable of expressing the oligopeptide in a host cell.

22. An in vitro method for measuring the level of antibody that binds to the oligopeptide of any one of paragraphs 1-20 in a sample, the method comprising providing said oligopeptide immobilized on a substrate, bringing the sample and the substrate into contact with each other, and measuring the level of antibody bound to the substrate.

23. The in vitro method according to paragraph 22, wherein the oligopeptide is conjugated to a first member of a specific binding pair and wherein the substrate comprises a second member of the specific binding pair, such that the oligopeptide immobilized on the substrate has been prepared by bringing the first member and the second member of the specific binding pair into contact with each other.

24. The in vitro method according to paragraph 23, wherein the specific binding pair is comprised of (i) biotin and (ii) streptavidin or a protein that is functionally equivalent to streptavidin because it is also capable of binding biotin.

25. The in vitro method according to paragraph 24, wherein the first member of the specific binding pair is biotin.

26. The in vitro method according to any one of paragraphs 22-25, wherein the substrate is an ELISA plate.

27. The in vitro method according to any one of paragraphs 22-25, wherein the substrate is a magnetic bead.

28. The in vitro method according to any one of paragraphs 22-27, wherein the sample is a serum sample that has been obtained from a human subject.

29. The in vitro method according to any one of paragraphs 22-28, wherein the subject is a male subject and wherein the oligopeptide has a sequence that is selected from the group consisting of:

```
                                        (SEQ ID NO: 21)
RVPGCAHHADSLYTYPV, (SEQ ID NO: 23)
RDSANIYHADSLKGRFT, (SEQ ID NO: 29)
RVPGCAHHADSL,
and (SEQ ID NO: 31)
RDSANIYHADSL.
```

30. The in vitro method according to any one of paragraphs 22-28, wherein the subject is a female subject and wherein the oligopeptide has a sequence that is selected from the group consisting of:

```
                                        (SEQ ID NO: 20)
RGSRGQHQAHSLERVCH, (SEQ ID NO: 22)
RHSDEHHHDDSLPHPQQ, (SEQ ID NO: 28)
RGSRGQHQAHSL,
and (SEQ ID NO: 30)
RHSDEHHHDDSL.
```

31. The in vitro method according to any one of paragraphs 22-30, further comprising the step of comparing the level of antibody that binds the oligopeptide of any one of paragraphs 1-20 with a control level which is representative of the level of antibody that binds the oligopeptide in a healthy subject.

32. The in vitro method according to paragraph 31, wherein the pH of the sample is buffered to a pH of approximately 7.4 before it is brought into contact with the substrate.

33. The in vitro method according to paragraph 32, wherein a lower level of antibody that binds the oligopeptide in the sample, compared with the control level, is indicative of a demyelinating disease such as multiple sclerosis (MS).

34. The in vitro method according to paragraph 31, wherein the pH of the sample is buffered to a pH of approximately 7.1 before it is brought into contact with the substrate.

35. The in vitro method according to paragraph 34, wherein a higher level of antibody that binds the oligopeptide in the sample, compared with the control level, is indicative of a demyelinating disease such as multiple sclerosis (MS).

36. The in vitro method according to any one of paragraphs 22-35, wherein the method comprises measuring the level of antibody that binds a first oligopeptide of any one of paragraphs 1-20, and wherein the method further comprises measuring the level of antibody that binds a second oligopeptide of any one of paragraphs 1-20.

37. A kit for performing the in vitro method according to any one of paragraphs 22-36.

38. A method of inducing a demyelinating disease in a non-human animal, the method comprising administering to the non-human animal an oligopeptide according to any one of paragraphs 1-20 and an adjuvant.

39. The method according to paragraph 38, wherein the adjuvant is Freund's complete adjuvant.

40. The method according to paragraph 38 or paragraph 39, wherein the oligopeptide and the adjuvant are administered at the same time.

41. The method according to any one of paragraphs 38-40, wherein the oligopeptide and the adjuvant are administered by intradermal injection.
42. The method according to any one of paragraphs 38-41, wherein the demyelinating disease is characteristic of multiple sclerosis (MS).
43. The method according to any one of paragraphs 38-42, wherein plaque formation is induced without substantial damage to the blood brain barrier (BBB).
44. The method according to any one of paragraphs 38-42, wherein the method also comprises administering Pertussis toxin to the non-human animal.
45. The method according to any one of paragraphs 38-44, wherein the non-human animal is a mouse, a guinea pig, a dog, a cow, or a chicken.
46. An oligopeptide according to any one of paragraphs 1-20, for use as a medicament.
47. An oligopeptide according to any one of paragraphs 1-20, for use in diagnostics.
48. An oligopeptide according to any one of paragraphs 1-20, for use in a method of treating a demyelinating disease in a subject, the method comprising administering the oligopeptide to the subject
49. The oligopeptide for the use according to paragraph 48, wherein the demyelinating disease is multiple sclerosis (MS).
50. The oligopeptide for the use according to paragraph 48 or paragraph 49, wherein the oligopeptide is administered intravenously, orally, intranasally or via an aerosol.
51. A method of treating a demyelinating disease, wherein the method is defined by any one of paragraphs 48-50.
52. An antibody that specifically binds to the oligopeptide of any one of paragraphs 1-51.
53. The antibody of paragraph 52, wherein the antibody is a monoclonal antibody.

REFERENCES

All publications, patent and patent applications cited herein or filed with this application, including references filed as part of an Information Disclosure Statement are incorporated by reference in their entirety.
1. Mackenzie I S, Morant S V, Bloomfield G a, MacDonald T M, O'Riordan J. Incidence and prevalence of multiple sclerosis in the UK 1990-2010: a descriptive study in the General Practice Research Database. J Neurol Neurosurg Psychiatry. 2014; 85(1):76-84.
2. MS Trust UK: Prevalence and incidence of multiple sclerosis [Internet]. 2015 [cited 2016 Jun. 20]. Available from: www.mstrust.org.uk
3. Correale J, Farez M F. The role of astrocytes in multiple sclerosis progression. Front Neurol. 2015; 6(August):1-12.
4. Ludwin S K, Rao V T, Moore C S, Antel J P. Astrocytes in multiple sclerosis. Mult Scler J. 2016; 1-11.
5. Pender M P, Burrows S R. Epstein-Barr virus and multiple sclerosis: potential opportunities for immunotherapy. Clin Transl Immunol.2014; 3(10):e27.
6. Mix E, Meyer-Rienecker H, Hartung H P, Zettl U K. Animal models of multiple sclerosis-Potentials and limitations. Prog Neurobiol. 2010; 92(3):386-404.
7. Ransohoff R M. Animal models of multiple sclerosis: the good, the bad and the bottom line. Nat Neurosci. 2012; 15(8):1074-7.
8. He Y-X, Du M, Shi H-L, Huang F, Liu H-S, Wu H, et al. Astragalosides from Radix Astragali benefits experimental autoimmune encephalomyelitis in C57BL/6 mice at multiple levels. BMC Complement Altern Med. 2014; 14:313.
9. Pachner A R. Experimental models of multiple sclerosis. Curr Opin Neurol. 2011; 24(3):291-9.
10. La Mantia L, Di Pietrantonj C, Rovaris M, Rigon G, Frau S, Berardo F, et al. Comparative efficacy of interferon β versus glatiramer acetate for relapsing-remitting multiple sclerosis. Cochrane database Syst Rev. 2014; 7:1-5.
11. Fridkis-Hareli M, Aharoni R, Teitelbaum D, Amon R, Sela M, Strominger J L. Binding of random copolymers of three amino acids to class II MHC molecules. Int Immunol. 1999; 11(5):635-41.
12. Drozdowski W. Does interferon beta therapy affect survival of multiple sclerosis patients? Neurol Neurochir Pol. 2014; 48(6):436-41.
13. Timmerman P, Van Dijk E, Puijk W, Schaaper W, Slootstra J, Carlisle S J, et al. Mapping of a discontinuous and highly conformational binding site on follicle stimulating hormone subunit-β (FSH-β) using domain Scan™ and Matrix Scan™ technology. Mol Divers. 2004; 8(2):61-77.
14. Tomassini V. Sex hormones modulate brain damage in multiple sclerosis: MRI evidence. J Neurol Neurosurg Psychiatry. 2005; 76(2):272-5.
15. Gobert B, Jolivet-Reynaud C, Dalbon P, Barbarino-Monnier P, Faure G C, Jolivet M, et al. An immunoreactive peptide of the FSH involved in autoimmune infertility. Biochem Biophys Res Commun. 2001; 289(4):819-24.
16. Opsahl M L, Kennedy P G E. Early and late HHV-6 gene transcripts in multiple sclerosis lesions and normal appearing white matter. Brain. 2005; 128(3):516-27.
17. FT S, J L F, Olsson T. Anti-myelin basic protein and anti-proteolipid protein antibody-secreting cells in the cerebrospinal fluid of patients with acute optic neuritis. Arch Neurol. 1994; 51(10):1032-6.
18. Lazzarini R A. Myelin Biology and Disorders. Robert A. Lazzarini, John W. Griffin, Hans Lassman, Klaus-Armin Nave R M and BDT, editor. Vol. 1. Elsevier; 2004. 1600 p.
19. David Male, Jonathan Brostoff, David B. Roth I R. Immunological Tolerance. Immunology. 8th ed. Elsevier; 2012. p. 307-21.
20 Hudson, L. D. (2004). Chapter 33: Multiple Sclerosis: Therapy. In L. RA (Ed.), Myelin Biology and Disorders (p. 796-798). Elsevier

The invention claimed is:

1. An in vitro method for detecting multiple sclerosis (MS) in a subject, the method comprising contacting an oligopeptide immobilized on a substrate with a sample obtained from the subject, and measuring a level of an antibody bound to the oligopeptide immobilized on the substrate, wherein the oligopeptide comprises up to 30 amino acid residues comprising an amino acid sequence RXSXXXXHADSL (SEQ ID NO: 51) or RXPXXXXHADSL (SEQ ID NO: 52).

2. The in vitro method according to claim 1, wherein the oligopeptide has 12-17 amino acids.

3. The in vitro method according to claim 1, wherein the amino acid sequence of the oligopeptide consists of RXSXXXXHADSLXXXXX (SEQ ID NO: 53) or RXPXXXXHADSLXXXXX (SEQ ID NO 54).

4. The in vitro method according to claim 1, wherein the amino acid sequence of the oligopeptide is selected from the group consisting of:

RVPGCAHHADSLYTYPV, (SEQ ID NO: 21)

RDSANIYHADSLKGRFT, (SEQ ID NO: 23)

RMSTPNPHADSL, (SEQ ID NO: 25)

RVPGCAHHADSL, (SEQ ID NO: 29)
and

RDSANIYHADSL. (SEQ ID NO: 31)

5. The in vitro method according to claim 1, wherein the oligopeptide is conjugated to a first member of a specific binding pair,
wherein the substrate comprises a second member of the specific binding pair, and
wherein the oligopeptide is immobilized on the substrate by contact between the first member and the second member of the specific binding pair.

6. The in vitro method according to claim 5, wherein the specific binding pair comprises (i) biotin and (ii) streptavidin or a protein capable of binding biotin.

7. The in vitro method according to claim 6, wherein the first member of the specific binding pair comprises biotin.

8. The in vitro method according to claim 1, wherein the substrate comprises an ELISA plate or a magnetic bead.

9. The in vitro method according to claim 1, wherein the sample comprises a serum sample of a human subject.

10. The in vitro method according to claim 1, wherein the subject is a male subject, and wherein the oligopeptide comprises a sequence selected from the group consisting of:

RVPGCAHHADSLYTYPV, (SEQ ID NO: 21)

RDSANIYHADSLKGRFT, (SEQ ID NO: 23)

RVPGCAHHADSL, (SEQ ID NO: 29)
and

RDSANIYHADSL. (SEQ ID NO: 31)

11. The in vitro method according to claim 1, further comprising comparing the level of the antibody bound to the oligopeptide with a control level,
wherein the control level is representative of a level of antibody in a sample of a healthy subject that binds the oligopeptide.

12. The in vitro method according to claim 11, wherein a pH of the sample of the subject is buffered to approximately 7.4 before the sample of the subject is brought into contact with the substrate.

13. The in vitro method according to claim 12, wherein a lower level of an antibody bound to the oligopeptide in the sample, compared with the control level, indicates a demyelinating disease.

14. The in vitro method according to claim 11, wherein a pH of the sample of the subject is buffered to approximately 7.1 before the sample of the subject is brought into contact with the substrate.

15. The in vitro method according to claim 14, wherein a higher level of an antibody bound to the oligopeptide in the sample, compared with the control level, indicates a demyelinating disease.

16. The in vitro method according to claim 1, wherein the oligopeptide immobilized on a substrate is a first oligopeptide, further comprising measuring a level of an antibody bound to a second oligopeptide,
wherein the second oligopeptide comprises up to 30 amino acid residues comprising an amino acid sequence RXSXXXXHADSL (SEQ ID NO: 51) or RXPXXXXHADSL (SEQ ID NO: 52), and
wherein the amino acid sequence of the second oligopeptide is different compared to the amino acid sequence of the first oligopeptide.

* * * * *

SEQUENCE LISTING

```
<160> NUMBER OF SEQ ID NOS: 58

<210> SEQ ID NO 1
<211> LENGTH: 4
<212> TYPE: PRT
```

```
<213> ORGANISM: Artificial Sequence
<220> FEATURE:
<223> OTHER INFORMATION: oligopeptide motif
<220> FEATURE:
<221> NAME/KEY: MISC_FEATURE
<222> LOCATION: (1)..(1)
<223> OTHER INFORMATION: Xaa is either Ala or Asp
<220> FEATURE:
<221> NAME/KEY: MISC_FEATURE
<222> LOCATION: (2)..(2)
<223> OTHER INFORMATION: Xaa is either Asp or His

<400> SEQUENCE: 1

Xaa Xaa Ser Leu
1

<210> SEQ ID NO 2
<211> LENGTH: 4
<212> TYPE: PRT
<213> ORGANISM: Artificial Sequence
<220> FEATURE:
<223> OTHER INFORMATION: oligopeptide motif
<220> FEATURE:
<221> NAME/KEY: MOD_RES
<222> LOCATION: (2)..(2)
<223> OTHER INFORMATION: Xaa is either Asp or His

<400> SEQUENCE: 2

Ala Xaa Ser Leu
1

<210> SEQ ID NO 3
<211> LENGTH: 4
<212> TYPE: PRT
<213> ORGANISM: Artificial Sequence
<220> FEATURE:
<223> OTHER INFORMATION: oligopeptide motif
<220> FEATURE:
<221> NAME/KEY: MISC_FEATURE
<222> LOCATION: (2)..(2)
<223> OTHER INFORMATION: Xaa is either Asp or His

<400> SEQUENCE: 3

Asp Xaa Ser Leu
1

<210> SEQ ID NO 4
<211> LENGTH: 4
<212> TYPE: PRT
<213> ORGANISM: Artificial Sequence
<220> FEATURE:
<223> OTHER INFORMATION: oligopeptide motif

<400> SEQUENCE: 4

Ala Asp Ser Leu
1

<210> SEQ ID NO 5
<211> LENGTH: 4
<212> TYPE: PRT
<213> ORGANISM: Artificial Sequence
<220> FEATURE:
<223> OTHER INFORMATION: oligopeptide motif

<400> SEQUENCE: 5

Ala His Ser Leu
1

<210> SEQ ID NO 6
```

```
<211> LENGTH: 4
<212> TYPE: PRT
<213> ORGANISM: Artificial Sequence
<220> FEATURE:
<223> OTHER INFORMATION: oligopeptide motif

<400> SEQUENCE: 6

Asp Asp Ser Leu
1

<210> SEQ ID NO 7
<211> LENGTH: 12
<212> TYPE: PRT
<213> ORGANISM: Artificial Sequence
<220> FEATURE:
<223> OTHER INFORMATION: oligopeptide motif
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is either Ala or Asp
<220> FEATURE:
<221> NAME/KEY: MISC_FEATURE
<222> LOCATION: (10)..(10)
<223> OTHER INFORMATION: Xaa is either Asp or His

<400> SEQUENCE: 7

Arg Xaa Xaa Xaa Xaa Xaa Xaa Xaa Xaa Xaa Ser Leu
1               5                   10

<210> SEQ ID NO 8
<211> LENGTH: 5
<212> TYPE: PRT
<213> ORGANISM: Artificial Sequence
<220> FEATURE:
<223> OTHER INFORMATION: oligopeptide motif
<220> FEATURE:
<221> NAME/KEY: MISC_FEATURE
<222> LOCATION: (2)..(2)
<223> OTHER INFORMATION: Xaa is either Ala or Asp
<220> FEATURE:
<221> NAME/KEY: MISC_FEATURE
<222> LOCATION: (3)..(3)
<223> OTHER INFORMATION: Xaa is either Asp or His

<400> SEQUENCE: 8

His Xaa Xaa Ser Leu
1               5

<210> SEQ ID NO 9
<211> LENGTH: 5
<212> TYPE: PRT
<213> ORGANISM: Artificial Sequence
<220> FEATURE:
<223> OTHER INFORMATION: oligopeptide motif
<220> FEATURE:
<221> NAME/KEY: MISC_FEATURE
<222> LOCATION: (2)..(2)
<223> OTHER INFORMATION: Xaa is Ala or Asp
<220> FEATURE:
<221> NAME/KEY: MISC_FEATURE
<222> LOCATION: (3)..(3)
<223> OTHER INFORMATION: Xaa is Asp or His

<400> SEQUENCE: 9

Gln Xaa Xaa Ser Leu
1               5
```

```
<210> SEQ ID NO 10
<211> LENGTH: 12
<212> TYPE: PRT
<213> ORGANISM: Artificial Sequence
<220> FEATURE:
<223> OTHER INFORMATION: oligopeptide motif
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is Ala or Asp
<220> FEATURE:
<221> NAME/KEY: MISC_FEATURE
<222> LOCATION: (10)..(10)
<223> OTHER INFORMATION: Xaa is Asp or His

<400> SEQUENCE: 10

Arg Xaa Xaa Xaa Xaa Xaa Xaa His Xaa Xaa Ser Leu
1               5                   10

<210> SEQ ID NO 11
<211> LENGTH: 12
<212> TYPE: PRT
<213> ORGANISM: Artificial Sequence
<220> FEATURE:
<223> OTHER INFORMATION: oligopeptide motif
<220> FEATURE:
<221> NAME/KEY: misc_feature
<222> LOCATION: (2)..(7)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is Ala or Asp
<220> FEATURE:
<221> NAME/KEY: MISC_FEATURE
<222> LOCATION: (10)..(10)
<223> OTHER INFORMATION: Xaa is Asp or His

<400> SEQUENCE: 11

Arg Xaa Xaa Xaa Xaa Xaa Xaa Gln Xaa Xaa Ser Leu
1               5                   10

<210> SEQ ID NO 12
<211> LENGTH: 5
<212> TYPE: PRT
<213> ORGANISM: Artificial Sequence
<220> FEATURE:
<223> OTHER INFORMATION: oligopeptide motif
<220> FEATURE:
<221> NAME/KEY: MISC_FEATURE
<222> LOCATION: (1)..(1)
<223> OTHER INFORMATION: Xaa is Ala or Asp
<220> FEATURE:
<221> NAME/KEY: MISC_FEATURE
<222> LOCATION: (2)..(2)
<223> OTHER INFORMATION: Xaa is Asp or His

<400> SEQUENCE: 12

Xaa Xaa Ser Leu Glu
1               5

<210> SEQ ID NO 13
<211> LENGTH: 6
<212> TYPE: PRT
<213> ORGANISM: Artificial Sequence
<220> FEATURE:
<223> OTHER INFORMATION: oligopeptide motif
<220> FEATURE:
<221> NAME/KEY: MISC_FEATURE
```

```
<222> LOCATION: (1)..(1)
<223> OTHER INFORMATION: Xaa is Ala or Asp
<220> FEATURE:
<221> NAME/KEY: MISC_FEATURE
<222> LOCATION: (2)..(2)
<223> OTHER INFORMATION: Xaa is Asp or His
<220> FEATURE:
<221> NAME/KEY: misc_feature
<222> LOCATION: (5)..(5)
<223> OTHER INFORMATION: Xaa can be any naturally occurring amino acid

<400> SEQUENCE: 13

Xaa Xaa Ser Leu Xaa Arg
1               5

<210> SEQ ID NO 14
<211> LENGTH: 10
<212> TYPE: PRT
<213> ORGANISM: Artificial Sequence
<220> FEATURE:
<223> OTHER INFORMATION: oligopeptide motif
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is Ala or Asp
<220> FEATURE:
<221> NAME/KEY: MISC_FEATURE
<222> LOCATION: (8)..(8)
<223> OTHER INFORMATION: Xaa is Asp or His

<400> SEQUENCE: 14

Ser Xaa Xaa Xaa Xaa Xaa Xaa Xaa Ser Leu
1               5                   10

<210> SEQ ID NO 15
<211> LENGTH: 10
<212> TYPE: PRT
<213> ORGANISM: Artificial Sequence
<220> FEATURE:
<223> OTHER INFORMATION: oligopeptide motif
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is Ala or Asp
<220> FEATURE:
<221> NAME/KEY: MISC_FEATURE
<222> LOCATION: (8)..(8)
<223> OTHER INFORMATION: Xaa is Asp or His

<400> SEQUENCE: 15

Pro Xaa Xaa Xaa Xaa Xaa Xaa Xaa Ser Leu
1               5                   10

<210> SEQ ID NO 16
<211> LENGTH: 4
<212> TYPE: PRT
<213> ORGANISM: Artificial Sequence
<220> FEATURE:
<223> OTHER INFORMATION: oligopeptide motif

<400> SEQUENCE: 16

Asp His Ser Leu
1
```

```
<210> SEQ ID NO 17
<211> LENGTH: 17
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is Ala or Asp
<220> FEATURE:
<221> NAME/KEY: MISC_FEATURE
<222> LOCATION: (10)..(10)
<223> OTHER INFORMATION: Xaa is Asp or His
<220> FEATURE:
<221> NAME/KEY: misc_feature
<222> LOCATION: (13)..(17)
<223> OTHER INFORMATION: Xaa can be any naturally occurring amino acid

<400> SEQUENCE: 17

Arg Xaa Xaa Xaa Xaa Xaa Xaa Xaa Xaa Xaa Ser Leu Xaa Xaa Xaa Xaa
1               5                   10                  15

Xaa

<210> SEQ ID NO 18
<211> LENGTH: 17
<212> TYPE: PRT
<213> ORGANISM: Artificial Sequence
<220> FEATURE:
<223> OTHER INFORMATION: Oligopeptide motif

<400> SEQUENCE: 18

Arg Leu Thr Leu Ser Pro Glu Gln Ala His Ser Leu Ile Leu Gln His
1               5                   10                  15

Leu

<210> SEQ ID NO 19
<211> LENGTH: 16
<212> TYPE: PRT
<213> ORGANISM: Artificial Sequence
<220> FEATURE:
<223> OTHER INFORMATION: Oligopeptide motif

<400> SEQUENCE: 19

Met Pro Arg Thr Gln Glu Asn Ala His Ser Leu Glu Arg Cys Trp Leu
1               5                   10                  15

<210> SEQ ID NO 20
<211> LENGTH: 17
<212> TYPE: PRT
<213> ORGANISM: Artificial Sequence
<220> FEATURE:
<223> OTHER INFORMATION: Oligopeptide motif

<400> SEQUENCE: 20

Arg Gly Ser Arg Gly Gln His Gln Ala His Ser Leu Glu Arg Val Cys
1               5                   10                  15

His

<210> SEQ ID NO 21
<211> LENGTH: 17
<212> TYPE: PRT
<213> ORGANISM: Artificial Sequence
```

```
<220> FEATURE:
<223> OTHER INFORMATION: Oligopeptide  motif

<400> SEQUENCE: 21

Arg Val Pro Gly Cys Ala His His Ala Asp Ser Leu Tyr Thr Tyr Pro
1               5                   10                  15
Val

<210> SEQ ID NO 22
<211> LENGTH: 17
<212> TYPE: PRT
<213> ORGANISM: Artificial Sequence
<220> FEATURE:
<223> OTHER INFORMATION: Oligopeptide motif

<400> SEQUENCE: 22

Arg His Ser Asp Glu His His His Asp Asp Ser Leu Pro His Pro Gln
1               5                   10                  15
Gln

<210> SEQ ID NO 23
<211> LENGTH: 17
<212> TYPE: PRT
<213> ORGANISM: Artificial Sequence
<220> FEATURE:
<223> OTHER INFORMATION: Oligopeptide motif

<400> SEQUENCE: 23

Arg Asp Ser Ala Asn Ile Tyr His Ala Asp Ser Leu Lys Gly Arg Phe
1               5                   10                  15
Thr

<210> SEQ ID NO 24
<211> LENGTH: 17
<212> TYPE: PRT
<213> ORGANISM: Artificial Sequence
<220> FEATURE:
<223> OTHER INFORMATION: Oligopeptide motif

<400> SEQUENCE: 24

Arg Leu Gly Thr His Val Leu Glu Ala His Ser Leu Asp Lys Val Ser
1               5                   10                  15
His

<210> SEQ ID NO 25
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 25

Arg Met Ser Thr Pro Asn Pro His Ala Asp Ser Leu
1               5                   10

<210> SEQ ID NO 26
<211> LENGTH: 16
<212> TYPE: PRT
<213> ORGANISM: Artificial Sequence
<220> FEATURE:
<223> OTHER INFORMATION: oligopeptide motif

<400> SEQUENCE: 26

Ser Ser Pro Glu His Arg Leu Ala His Ser Leu Glu Arg Asp Tyr Gly
```

```
<210> SEQ ID NO 27
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 27

Arg Leu Thr Leu Ser Pro Glu Gln Ala His Ser Leu
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 28

Arg Gly Ser Arg Gly Gln His Gln Ala His Ser Leu
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 29

Arg Val Pro Gly Cys Ala His His Ala Asp Ser Leu
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 30

Arg His Ser Asp Glu His His Asp Asp Ser Leu
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 31

Arg Asp Ser Ala Asn Ile Tyr His Ala Asp Ser Leu
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 32

Arg Leu Gly Thr His Val Leu Glu Ala His Ser Leu
1               5                   10
```

<210> SEQ ID NO 33
<211> LENGTH: 12
<212> TYPE: PRT
<213> ORGANISM: Artificial Sequence
<220> FEATURE:
<223> OTHER INFORMATION: Oligopeptide motif

<400> SEQUENCE: 33

Arg Met Ser Thr Pro Asn Pro His Ala Asp Ser Leu
1               5                   10

<210> SEQ ID NO 34
<211> LENGTH: 6
<212> TYPE: PRT
<213> ORGANISM: Artificial Sequence
<220> FEATURE:
<223> OTHER INFORMATION: Oligopeptide motif
<220> FEATURE:
<221> NAME/KEY: MISC_FEATURE
<222> LOCATION: (1)..(1)
<223> OTHER INFORMATION: Xaa is Ala or Asp
<220> FEATURE:
<221> NAME/KEY: MISC_FEATURE
<222> LOCATION: (2)..(2)
<223> OTHER INFORMATION: Xaa is Asp or His

<400> SEQUENCE: 34

Xaa Xaa Ser Leu Glu Arg
1               5

<210> SEQ ID NO 35
<211> LENGTH: 14
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (2)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is Ala or Asp
<220> FEATURE:
<221> NAME/KEY: MISC_FEATURE
<222> LOCATION: (10)..(10)
<223> OTHER INFORMATION: Xaa is Asp or His

<400> SEQUENCE: 35

Arg Xaa Xaa Xaa Xaa Xaa Xaa Xaa Xaa Xaa Ser Leu Glu Arg
1               5                   10

<210> SEQ ID NO 36
<211> LENGTH: 5
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (2)..(2)
<223> OTHER INFORMATION: Xaa is Ala or Asp
<220> FEATURE:
<221> NAME/KEY: MISC_FEATURE
<222> LOCATION: (3)..(3)
<223> OTHER INFORMATION: Xaa is Asp or His

```
<400> SEQUENCE: 36

Xaa Xaa Xaa Ser Leu
1               5

<210> SEQ ID NO 37
<211> LENGTH: 6
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa is Ala or Asp
<220> FEATURE:
<221> NAME/KEY: MISC_FEATURE
<222> LOCATION: (4)..(4)
<223> OTHER INFORMATION: Xaa is Asp or His

<400> SEQUENCE: 37

Xaa Xaa Xaa Xaa Ser Leu
1               5

<210> SEQ ID NO 38
<211> LENGTH: 7
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(3)
<223> OTHER INFORMATION: Xaa can be any naturally occurring amino acid
<220> FEATURE:
<221> NAME/KEY: MISC_FEATURE
<222> LOCATION: (4)..(4)
<223> OTHER INFORMATION: Xaa is Ala or Asp
<220> FEATURE:
<221> NAME/KEY: MISC_FEATURE
<222> LOCATION: (5)..(5)
<223> OTHER INFORMATION: Xaa is Asp or His

<400> SEQUENCE: 38

Xaa Xaa Xaa Xaa Xaa Ser Leu
1               5

<210> SEQ ID NO 39
<211> LENGTH: 8
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa is Ala or Asp
<220> FEATURE:
<221> NAME/KEY: MISC_FEATURE
<222> LOCATION: (6)..(6)
<223> OTHER INFORMATION: Xaa is Asp or His

<400> SEQUENCE: 39

Xaa Xaa Xaa Xaa Xaa Xaa Ser Leu
```

```
<210> SEQ ID NO 40
<211> LENGTH: 9
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa is Ala or Asp
<220> FEATURE:
<221> NAME/KEY: MISC_FEATURE
<222> LOCATION: (7)..(7)
<223> OTHER INFORMATION: Xaa is Asp or His

<400> SEQUENCE: 40

Xaa Xaa Xaa Xaa Xaa Xaa Xaa Ser Leu
1               5

<210> SEQ ID NO 41
<211> LENGTH: 10
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa is Ala or Asp
<220> FEATURE:
<221> NAME/KEY: MISC_FEATURE
<222> LOCATION: (8)..(8)
<223> OTHER INFORMATION: Xaa is Asp or His

<400> SEQUENCE: 41

Xaa Xaa Xaa Xaa Xaa Xaa Xaa Xaa Ser Leu
1               5                   10

<210> SEQ ID NO 42
<211> LENGTH: 11
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa is Ala or Asp
<220> FEATURE:
<221> NAME/KEY: MISC_FEATURE
<222> LOCATION: (9)..(9)
<223> OTHER INFORMATION: Xaa is Asp or His

<400> SEQUENCE: 42

Xaa Xaa Xaa Xaa Xaa Xaa Xaa Xaa Xaa Ser Leu
1               5                   10

<210> SEQ ID NO 43
```

```
<211> LENGTH: 12
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (1)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa is Ala or Asp
<220> FEATURE:
<221> NAME/KEY: MISC_FEATURE
<222> LOCATION: (10)..(10)
<223> OTHER INFORMATION: Xaa is Asp or His

<400> SEQUENCE: 43

Xaa Xaa Xaa Xaa Xaa Xaa Xaa Xaa Xaa Xaa Ser Leu
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (2)..(8)
<223> OTHER INFORMATION: Xaa can be any naturally occurring amino acid

<400> SEQUENCE: 44

Arg Xaa Xaa Xaa Xaa Xaa Xaa Xaa Ala Asp Ser Leu
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (2)..(8)
<223> OTHER INFORMATION: Xaa can be any naturally occurring amino acid

<400> SEQUENCE: 45

Arg Xaa Xaa Xaa Xaa Xaa Xaa Xaa Ala His Ser Leu
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (2)..(8)
<223> OTHER INFORMATION: Xaa can be any naturally occurring amino acid

<400> SEQUENCE: 46

Arg Xaa Xaa Xaa Xaa Xaa Xaa Xaa Asp His Ser Leu
1               5                   10

<210> SEQ ID NO 47
<211> LENGTH: 12
<212> TYPE: PRT
<213> ORGANISM: Artificial Sequence
```

```
<220> FEATURE:
<223> OTHER INFORMATION: Oligopeptide motif
<220> FEATURE:
<221> NAME/KEY: misc_feature
<222> LOCATION: (2)..(8)
<223> OTHER INFORMATION: Xaa can be any naturally occurring amino acid

<400> SEQUENCE: 47

Arg Xaa Xaa Xaa Xaa Xaa Xaa Xaa Asp Asp Ser Leu
 1               5                  10

<210> SEQ ID NO 48
<211> LENGTH: 5
<212> TYPE: PRT
<213> ORGANISM: Artificial Sequence
<220> FEATURE:
<223> OTHER INFORMATION: Oligopeptide motif

<400> SEQUENCE: 48

His Ala Asp Ser Leu
 1               5

<210> SEQ ID NO 49
<211> LENGTH: 10
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (2)..(6)
<223> OTHER INFORMATION: Xaa can be any naturally occurring amino acid

<400> SEQUENCE: 49

Ser Xaa Xaa Xaa Xaa Xaa Ala Asp Ser Leu
 1               5                  10

<210> SEQ ID NO 50
<211> LENGTH: 10
<212> TYPE: PRT
<213> ORGANISM: Artificial Sequence
<220> FEATURE:
<223> OTHER INFORMATION: Oligopeptide motif
<220> FEATURE:
<221> NAME/KEY: misc_feature
<222> LOCATION: (2)..(6)
<223> OTHER INFORMATION: Xaa can be any naturally occurring amino acid

<400> SEQUENCE: 50

Pro Xaa Xaa Xaa Xaa Xaa Ala Asp Ser Leu
 1               5                  10

<210> SEQ ID NO 51
<211> LENGTH: 12
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid

<400> SEQUENCE: 51

Arg Xaa Ser Xaa Xaa Xaa Xaa His Ala Asp Ser Leu
 1               5                  10
```

```
<210> SEQ ID NO 52
<211> LENGTH: 12
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid

<400> SEQUENCE: 52

Arg Xaa Pro Xaa Xaa Xaa Xaa His Ala Asp Ser Leu
1               5                   10

<210> SEQ ID NO 53
<211> LENGTH: 17
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 53

Arg Xaa Ser Xaa Xaa Xaa Xaa His Ala Asp Ser Leu Xaa Xaa Xaa Xaa
1               5                   10                  15

Xaa

<210> SEQ ID NO 54
<211> LENGTH: 17
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 54

Arg Xaa Pro Xaa Xaa Xaa Xaa His Ala Asp Ser Leu Xaa Xaa Xaa Xaa
1               5                   10                  15

Xaa

<210> SEQ ID NO 55
<211> LENGTH: 13
```

```
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid

<400> SEQUENCE: 55

Arg Xaa Ser Xaa Xaa Xaa Xaa His Ala Asp Ser Leu Glu
1               5                   10

<210> SEQ ID NO 56
<211> LENGTH: 13
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid

<400> SEQUENCE: 56

Arg Xaa Pro Xaa Xaa Xaa Xaa His Ala Asp Ser Leu Glu
1               5                   10

<210> SEQ ID NO 57
<211> LENGTH: 14
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid

<400> SEQUENCE: 57

Arg Xaa Ser Xaa Xaa Xaa Xaa His Ala Asp Ser Leu Xaa Arg
1               5                   10

<210> SEQ ID NO 58
<211> LENGTH: 14
<212> TYPE: PRT
<213> ORGANISM: Artificial Sequence
<220> FEATURE:
<223> OTHER INFORMATION: oligopeptide
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(7)
<223> OTHER INFORMATION: Xaa can be any naturally occurring amino acid
```

```
<220> FEATURE:
<221> NAME/KEY: misc_feature
<222> LOCATION: (13)..(13)
<223> OTHER INFORMATION: Xaa can be any naturally occurring amino acid

<400> SEQUENCE: 58

Arg Xaa Pro Xaa Xaa Xaa Xaa His Ala Asp Ser Leu Xaa Arg
1               5                   10
```